US012758586B2

(12) United States Patent
Zhang et al.

(10) Patent No.: US 12,758,586 B2
(45) Date of Patent: Oct. 13, 2026

(54) VESICLE AND USE THEREOF

(71) Applicant: EV CELL BIOTECH (GUANGZHOU) CO., LTD., Guangzhou (CN)

(72) Inventors: Xiao Zhang, Guangzhou (CN); Xiaoxing Kou, Guangzhou (CN); Songtao Shi, Guangzhou (CN)

(73) Assignee: EV CELL BIOTECH (GUANGZHOU) CO., LTD., Guangzhou (CN)

( * ) Notice: Subject to any disclaimer, the term of this patent is extended or adjusted under 35 U.S.C. 154(b) by 934 days.

(21) Appl. No.: 17/793,860

(22) PCT Filed: Jan. 20, 2021

(86) PCT No.: PCT/CN2021/072938
§ 371 (c)(1),
(2) Date: Jul. 19, 2022

(87) PCT Pub. No.: WO2021/147923
PCT Pub. Date: Jul. 29, 2021

(65) Prior Publication Data

US 2023/0051925 A1 Feb. 16, 2023

(30) Foreign Application Priority Data

Jan. 20, 2020 (CN) ......................... 202010066154.6
Jan. 20, 2020 (CN) ......................... 202010066155.0

(51) Int. Cl.
*A61K 35/28* (2015.01)
*A61P 7/04* (2006.01)
*C12N 5/0775* (2010.01)

(52) U.S. Cl.
CPC ................ *A61K 35/28* (2013.01); *A61P 7/04* (2018.01); *C12N 5/0662* (2013.01)

(58) Field of Classification Search
None
See application file for complete search history.

(56) References Cited

U.S. PATENT DOCUMENTS

2014/0364588 A1 12/2014 Haugwitz et al.
2015/0086639 A1 3/2015 Huang
2017/0216364 A1 8/2017 Shi et al.
2018/0066307 A1 3/2018 Ter-Ovanesyan et al.
2018/0371418 A1 12/2018 Yang et al.
2019/0324023 A1* 10/2019 Ichikawa ......... G01N 33/54346
2021/0072247 A1* 3/2021 Hong ............... G01N 33/57438
2022/0184225 A1* 6/2022 Tilton ...................... C12N 7/00
2023/0152325 A1* 5/2023 Cukierman ...... G01N 33/57492 435/7.23
2024/0310363 A1* 9/2024 Vallabhajosyula .. C12Q 1/6883

FOREIGN PATENT DOCUMENTS

CN 106289926 A 1/2017
CN 106659740 A 5/2017
CN 109893515 A 6/2019
JP 2011-505850 A 3/2011

OTHER PUBLICATIONS

International Search Report of PCT/CN2021/072938 Apr. 23, 2021.
Written Opinion of International Searching Authority of PCT/CN2021/072938 Apr. 23, 2021.
Weng, Zhen et al. "Research Progress on the Detection and Identification of Exosomes and Their Role in Blood Coagulation". Modern Medical Journal, vol. 47, No. 5, May 31, 2019.
Lin, Mengsi et al. "Syntaxin4 is Involved in Transport Mechanism of Mouse Oocyte Cortical Granules". Journal of Reproductive Medicine, vol. 27, No. 8 Aug. 31, 2018.
Chiara A. Elia et al. "Intracerebral Injection of Extracellular Vesicles from Mesenchymal Stem Cells Exerts Reduced Aβ Plaque Burden in Early Stages of a Preclinical Model of Alzheimer's Disease" Cells, vol. 8, No. 9 Sep. 30, 2019.
Greening, D. W., Xu, R., Ji, H., Tauro, B. J., & Simpson, R. J. (2015). A protocol for exosome isolation and characterization: Evaluation of ultracentrifugation, density-gradient separation, and immunoaffinity capture methods. In A. Posch (Ed.), Proteomic Profiling: Methods and Protocols (pp. 179-209). (Methods in Molecular Biology; vol. 1295). Humana Press.
Xiaoliang Wang et al., "Applied Molecular Pharmacology", Peking Union Medical College Press, Sep. 30, 2015, 2nd ed., pp. 524-528 (15 pages).
Ping He et al., "Advances in the study of exosomes and other extracellular vesicles in pathogenic microorganisms", Journal of Pathogen Biology (China), Apr. 20, 2017, vol. 12, No. 4, pp. 384-389 (13 pages).
Qun Wu et al., "The expression of syntaxin 4 and co-interaction with SNAP-23 in human NK cells", Chinese Journal of Microbiology and Immunology, Mar. 30, 2004, vol. 24, No. 3, pp. 165-168 (8 pages).
Jia Yao et al., "Isolation and identification of human umbilical cord mesenchymal stem cells-derived microvesicles", Chin. J. Cell Stem Cell (Electronic Edition) Aug. 1, 2016, vol. 6, No. 4, pp. 221-227 (13 pages).

(Continued)

*Primary Examiner* — Michail A Belyavskyi
(74) *Attorney, Agent, or Firm* — Sughrue Mion, PLLC

(57) ABSTRACT

Provided are a vesicle and the use thereof. The vesicle is an induced vesicle, and the sources thereof include stem cells or somatic cells, and the possessed markers include Syntaxin 4. Compared with an exosome in mesenchymal stem cells, the vesicle can specifically express Syntaxin 4 and can be used to distinguish characteristic markers of MSC-derived vesicles and exosomes. The vesicle can play a procoagulant effect in vitro, can improve the bleeding tendency of mice with hemophilia after in vivo injection, and can be used for the treatment of improving the bleeding tendency of hemophilia. In addition, the vesicle can be expelled through the skin and hair.

16 Claims, 20 Drawing Sheets

(56) References Cited

OTHER PUBLICATIONS

Yuqing Song et al., "Functional characterization of anti-bacterial umbilical cord mesenchymal stem cells and its therapeutic effect on sepsis mice", Master Thesis, Third Medical University of Chinese Peoples' Liberation Army, Dec. 4, 2017 (67 pages).

Kaitlin Clark et al., "Placental Mesenchymal Stem Cell-Derived Extracellular Vesicles Promote Myelin Regeneration in an Animal Model of Multiple Sclerosis", Cells, Nov. 23, 2019, vol. 8, No. 1497 (16 pages).

Ruenn Chai Lai et al., "MSC secretes at least 3 EV types each with a unique permutation of membrane lipid, protein and RNA", Journal of Extracellular Vesicles, Feb. 2, 2016, vol. 5, No. 29828 (12 pages).

* cited by examiner

CD29

CD44

CD73

CD166

CD34

CD45

CD9

CD63

CD81 hBMMSC lEVs MC3T3-E1 lEVs

VESICLE AND USE THEREOF

CROSS-REFERENCE TO RELATED APPLICATION

This application is the national phase application of International Application No. PCT/CN2021/072938, filed Jan. 20, 2021, which claims priorities to Chinese Patent Applications No. 202010066154.6 and No. 202010066155.0, both filed on Jan. 20, 2020, in China National Intellectual Property Administration, and respectively entitled "Vesicle and Use thereof" and "Use of Vesicle in the Manufacture of Hemophilia Medicaments", of the contents of each of which are hereby incorporated by reference in its entirety.

TECHNICAL FIELD

The present disclosure belongs to the field of biomedicine, and relates to a vesicle and a use thereof.

BACKGROUND ART

Extracellular vesicles (EVs) are nanoscale carriers containing proteins, nucleic acids and various cytokines secreted by cells. Extracellular vesicles can act on target cells in an endocrine or paracrine manner, and play an important role in the process of substance transmission and information exchange between cells. It has been found that the information exchange mediated by extracellular vesicles is of great significance for regulation in the physiological or pathological process, involving immune regulation, tumor growth, angiogenesis, injury repair, etc. At present, studies in this field mainly focus on exosomes. Exosomes are extracellular vesicles with a diameter of about 30-150 nm, containing RNA, lipids, proteins, etc. Exosomes are widely involved in the various physiological/pathological regulations of the body, and can be used for diagnosis, treatment and prognosis assessment of a variety of diseases. So far, mesenchymal stem cells (MSCs) have been considered to be the most potent cells for producing exosomes. Numerous studies have found that MSCs-derived exosomes can mimic the biological function of MSCs, and play an important part in regulation in promoting cell growth and differentiation and repairing tissue defects. Therefore, cell vesicle therapy based on MSCs-derived exosomes has achieved remarkable development in recent years. However, current exosome-based cell vesicle therapies still have many problems, such as complex exosome extraction and purification, time-consuming, high requirements for equipment and reagents, low physiological exosome production, and so on, which limit the clinical transformation and application of exosome therapies.

Hemophilia is a series of inherited hemorrhagic disorders of coagulation dysfunction with the common feature of disorders in thromboplastin production, which prolongs the clotting time and causes a life-long tendency to bleed after a small injury, and even "spontaneous" bleeding in critically ill patients without apparent trauma. On May 11, 2018, the National Health Commission of the People's Republic of China and other five departments jointly developed the *First Catalog of Rare Diseases*, with hemophilia included. There are mainly three forms of hemophilia, namely hemophilia A, hemophilia B and hemophilia C. Hemophilia A, namely factor VIII clotting factor (VIII: C) deficiency, is a sex-linked recessive genetic disease that is transmitted in women and occurs in men. Hemophilia B, namely factor IX (FIX)

deficiency, is also sex-linked recessively inherited, and its incidence is less than that of hemophilia A. Hemophilia C, namely factor XI (FXI) deficiency, is a rare hemophilia with incomplete autosomal recessive inheritance. With respect to the incidence, hemophilia A is the most common one, accounting for 80%-85%, hemophilia B is 15%-20%, and hemophilia C is rare. Exogenous coagulation factor injection has long been used as the main intervention measure for treating hemophilia, but this method has many problems, such as high cost, short duration, and easy production of autoantibodies, and therefore cannot provide effective treatment.

SUMMARY OF THE INVENTION

In some embodiments, the present disclosure provides a vesicle derived from mesenchymal stem cells.

In some embodiments, the present disclosure provides a vesicle composition.

In some embodiments, the present disclosure provides a pharmaceutical composition including a vesicle and against hemophilia.

In some embodiments, the present disclosure provides a kit for screening or identifying or extracting a vesicle.

In some embodiments, the present disclosure provides a marker for a vesicle.

In some embodiments, the present disclosure provides a method for identifying or selecting vesicles using markers.

In some embodiments, the present disclosure provides a method for production of a vesicle.

In some embodiments, the present disclosure provides a vesicle derived from somatic cells or stem cells, wherein the vesicle is an included vesicle, and the vesicle has markers including Syntaxin 4.

In some embodiments, a method for treatment or prevention or amelioration of a disease or a complication of the disease in a subject, including administering to the subject an effective amount of the vesicle or the vesicle combination or the composition; the disease being a bleeding disorder. In some embodiments, the bleeding disorder includes bleeding due to deficiency of coagulation factors, decreased platelet count and/or functional defects. In some embodiments, the bleeding disorder includes hemophilia, lupus hemorrhage, or Chédiak-Higashi syndrome. In some embodiments, hemophilia includes hemophilia A, hemophilia B, or hemophilia C. In some embodiments, the disease is hemophilia A.

In some embodiments, the stem cells include totipotent stem cells and pluripotent stem cells.

In some embodiments, the stem cells include mesenchymal stem cells and induced pluripotent stem cells (IPSs).

In some embodiments, the somatic cells include osteoblast cell lines.

In some embodiments, the cells may be primary cultured cells, or may be existing or established cell lines.

In some embodiments, the cell line refers to an immortalized cell culture which is capable of propagating indefinitely in an appropriate fresh medium and space.

In some embodiments, the cells may be an established cell strain.

In some embodiments, the induced vesicle refers to a vesicle produced by inducing apoptosis of normally viable stem cells or somatic cells by external impacts.

In some embodiments, the induced vesicle is produced by inducing stem cells or apoptosis of stem cells by addition of Staurospora, ultraviolet irradiation, starvation, or thermal stress, or a combination of one or more thereof.

In some embodiments, the possessed markers of the vesicle further include one or more of Annexin V, Flotillin-1, Cadherin 11, and Integrin alpha 5.

In some embodiments, the vesicle has a combination of the markers Syntaxin 4, Annexin V, Flotillin-1, Cadherin 11, and Integrin alpha 5.

In some embodiments, the vesicle has a high expression of the markers Annexin V, Flotillin-1, Cadherin 11, Integrin alpha 5, and Syntaxin 4.

In some embodiments, the expression levels of the markers Annexin V, Flotillin-1, Cadherin 11, Integrin alpha 5, and Syntaxin 4 in the vesicle are higher than that in MSCs or exosomes.

In some embodiments, the expression levels of the markers Annexin V, Flotillin-1, Cadherin 11, Integrin alpha 5, and Syntaxin 4 in the vesicle are about 1-2 fold, 2-3 fold, 1-3 fold, 3-4 fold and 3-6 fold, respectively, of that in exosomes derived from mesenchymal stem cells.

In some embodiments, the expression levels of the markers Annexin V, Flotillin-1, Cadherin 11, Integrin alpha 5, and Syntaxin 4 in the vesicle are about 1.5-2 fold, 2.5-3 fold, 1.5-2.5 fold, 3.5-4 fold and 3.5-5 fold, respectively, of that in exosomes derived from mesenchymal stem cells.

In some embodiments, the expression levels of the markers Annexin V, Flotillin-1, Cadherin 11, Integrin alpha 5, and Syntaxin 4 in the vesicle are about 1.5-1.9 fold, 2.5-2.9 fold, 1.8-2.5 fold, 3.5-3.9 fold and 4-5 fold, respectively, of that in exosomes derived from mesenchymal stem cells.

In some embodiments, the expression levels of the markers Annexin V, Flotillin-1, Cadherin 11, Integrin alpha 5, and Syntaxin 4 in the vesicle are 1.76 fold, 2.81 fold, 2.41 fold, 3.68 fold and 4.45 fold, respectively, of that in exosomes derived from mesenchymal stem cells.

In some embodiments, the exosome does not express Syntaxin 4, while the vesicle of the present disclosure expresses Syntaxin 4.

In some embodiments, the exosome does not simultaneously express Annexin V, Flotillin-1, Cadherin 11, Integrin alpha 5, and Syntaxin 4, while the vesicle of the present disclosure simultaneously expresses Annexin V, Flotillin-1, Cadherin 11, Integrin alpha 5, and Syntaxin 4.

In some embodiments, the vesicle and the exosomes are derived from mesenchymal stem cells of the same source.

In some embodiments, the surface membrane proteins of IEVs are analyzed by flow cytometry, and the results show that IEVs derived from MSCs can express similar surface proteins as MSCs, i.e., CD29, CD44, CD73, CD166 positive, and CD34, CD45 negative; at the same time, IEVs can express the ubiquitous surface proteins CD9, CD63, CD81 and C1q of extracellular vesicles.

In some embodiments, the induced vesicle is produced by inducing apoptosis of mesenchymal stem cells by the addition of staurosporine, ultraviolet irradiation, starvation, thermal stress, or a combination thereof.

In some embodiments, the vesicle is produced by inducing mesenchymal stem cells with staurosporine.

In some embodiments, the passage number of the mesenchymal stem cells may be about 2-5 passages, but is not limited thereto.

In some embodiments, the concentration of staurosporine is in a range of about 1-10000 nM. In some embodiments, the concentration of staurosporine is in a range of about 100-10000 nM. In some embodiments, the concentration of staurosporine is in a range of about 500-10000 nM. In some embodiments, the concentration of staurosporine is in a range of about 500-1000 nM. In some embodiments, the concentration of staurosporine is in a range of about 500-900 nM. In some embodiments, the concentration of staurosporine is in a range of about 500-800 nM.

In some embodiments, the vesicle has a diameter of about 0.03-6 μM. In some embodiments, the vesicle has a diameter of about 0.03-4.5 μM. In some embodiments, the vesicle has a diameter of about 0.03-1 μM. In some embodiments, the vesicle has a diameter of about 0.04-1 μM. In some embodiments, the vesicle has a diameter of about 0.05-1 μM. In some embodiments, the vesicle has a diameter of about 0.1-1 μM. In some embodiments, the vesicle has a diameter of about 0.15-1 μM.

In some embodiments, the present disclosure provides a vesicle combination including the vesicle described above.

In some embodiments, the vesicle combination further includes other prior art vesicles, including, but not limited to, exosomes, migrants, microbubbles, and ectosomes, for example.

In some embodiments, the proportion by count of the vesicle in the vesicle combination is about 65-100%.

In some embodiments, the proportion by count of the vesicle in the vesicle combination is about 75-98%.

In some embodiments, the proportion by count of the vesicle in the vesicle combination is about 80-96%.

In some embodiments, the present disclosure provides a composition including the vesicle described above, or the vesicle combination described above.

In some embodiments, the composition includes drugs, foods, health products, cosmetics, additives, or intermediates.

In some embodiments, the composition is a drug.

In some embodiments, the composition further includes a pharmaceutically or immunologically acceptable carrier.

In some embodiments, the composition is in a form selected from the group consisting of a lyophilized powder, an injection, a tablet, a capsule, a kit, or a patch.

In some embodiments, the vesicle is used as a drug carrier.

In some embodiments, the present disclosure provides a reagent or kit for screening or identification or extraction of the vesicle, including detection reagents for one or more of markers Annexin V, Flotillin-1, Cadherin 11, Integrin alpha 5, and Syntaxin 4.

In some embodiments, the detection reagents for the markers detect the expression levels of genes of the markers.

In some embodiments, the detection reagents for the markers detect the expression levels of mRNAs of the markers.

In some embodiments, the detection reagents for the markers detect the expression levels of proteins of the markers.

In some embodiments, the detection reagents for the markers are one or more of fluorescent quantitative PCR dyes, fluorescent quantitative PCR primers, fluorescent quantitative PCR probes, antibodies, antibody functional fragments, and conjugated antibodies.

In some embodiments, the kit is selected from one or more of a qPCR kit, an immunoblot assay kit, a flow cytometry assay kit, an immunohistochemical assay kit, and an ELISA kit.

In some embodiments, the kit is selected from a flow cytometry assay kit.

In some embodiments, the present disclosure also provides the use of the vesicle, or the vesicle composition, or the pharmaceutical composition in the preparation of a product for treatment or prevention or amelioration of a disease or a complication of the disease; such disease including liver diseases, and hemophilia.

In some embodiments, the disease is hemophilia, and the vesicle can play a procoagulant effect in vitro, can improve the bleeding tendency of mice with hemophilia after in vivo injection, and can be used for the treatment of improving the bleeding tendency of hemophilia, providing good application prospects.

In some embodiments, the disease is hemophilia A.

In some embodiments, the product includes drugs, foods, health products, cosmetics, additives, or intermediates.

In use of the vesicle for disease treatment, the vesicle may optionally be administered in a route selected from the group consisting of intravenous injection, intramuscular injection, subcutaneous injection, intrathecal injection or infusion, and intraorgan infusion. For example, for intravenous injection, tail vein injection may be used. Intraorgan infusion includes infusion into anatomical spaces such as, by way of example, the gall bladder, gastrointestinal lumen, esophagus, pulmonary system (by inhalation), and/or bladder.

As an example, for intraperitoneal injection in gastrointestinal infusion, the same therapeutic effect can also be obtained by intraperitoneal injection as compared with tail vein injection. Intraperitoneal injection is superior to tail vein injection in safety and maneuverability.

In some embodiments, the present disclosure also provides a method for selecting or identifying the vesicle, including detecting one or more of the following markers: Annexin V, Flotillin-1, Cadherin 11, Integrin alpha 5, and Syntaxin 4.

When the detection result shows positive for the markers, the vesicle is identified.

In some embodiments, the expressions of the markers may be compared to a control, and the result is positive when the expression level is significantly higher than that of the control. The control may be other existing vesicles or exosomes (may include one or more of exosomes, migrants, microbubbles, and ectosomes); other vesicles or exosomes may be derived from mesenchymal stem cells.

Among the markers, the marker Syntaxin is particularly preferred. In some embodiments, the vesicle (e.g. an induced vesicle) is identified when the expression level of Syntaxin 4 in a test vesicle is greater than or equal to 2-6 fold (more preferably 4-5 fold) of that in an exosome (e.g. an exosome from the same cell source).

In some embodiments, the present disclosure provides use of a detection reagent for a marker in the preparation of a reagent or kit for detection or identification of a vesicle, in which the markers include one or more of Annexin V, Flotillin-1, Cadherin 11, Integrin alpha 5, and Syntaxin 4, and the reagent or kit further includes a control reagent which includes one or more of exosomes, migrants, microbubbles, and ectosomes, and when the expression levels of the markers in the test sample is higher than that in the control reagent, the result is positive.

In some embodiments, the control agent is an exosome.

In some embodiments, the vesicle (e.g. an induced vesicle) is identified when the expression level of Syntaxin 4 in the test sample is greater than or equal to 2-6 fold of that in the exosome.

In some embodiments, the vesicle (e.g. an induced vesicle) is identified when the expression level of Syntaxin 4 in the test sample is greater than or equal to 4-5 fold of that in the exosome.

In some embodiments, the present disclosure provides a method for production of the vesicle described above, including inducing stem cells or somatic cells to produce the vesicle with an apoptosis-inducing agent agent.

In some embodiments, the method includes following steps: (1) culturing mesenchymal stem cells; (2) collecting the culture supernatant of the mesenchymal stem cells; and (3) separating a vesicle from the culture supernatant in step (2).

In some embodiments, the step of culturing mesenchymal stem cells in step (1) includes: (4) separating mesenchymal stem cells from a tissue; and (5) adding a culture medium to culture the mesenchymal stem cells; and contacting the mesenchymal stem cells in the culture medium with the apoptosis inducing agent.

In some embodiments, the apoptosis-inducing agent includes staurosporine, ultraviolet irradiation, starvation, or thermal stress, or a combination of one or more thereof.

In some embodiments, the apoptosis-inducing agent is staurosporine.

In some embodiments, the concentration of staurosporine is in a range of about 500-1000 nM. In some embodiments, the concentration of staurosporine is in a range of about 500-900 nM. In some embodiments, the concentration of staurosporine is in a range of about 500-800 nM.

In some embodiments, the cells are treated with the apoptosis inducing agent in step (5) for about 16-24 hours.

In some embodiments, in step (3), separating a vesicle includes separating a vesicle by ultracentrifugation.

In some embodiments, a single MSCs in the present disclosure is capable of yielding 300-2000 vesicles.

In some embodiments, the step of separating a vesicle by ultracentrifugation includes: (a) performing a first centrifugation on the collected culture supernatant, and taking the supernatant; (b) performing a second centrifugation on the supernatant collected in step (a), and taking the supernatant; (c) performing a third centrifugation on the supernatant collected in step (b), and taking the pellet; (d) performing a fourth centrifugation on the pellet collected in step (c), and taking the pellet; and (e) performing a fifth centrifugation on the pellet collected in step (c), and taking the pellet.

In some embodiments, the first centrifugation is performed at about 500-1500 g for 5-30 min. In some embodiments, the first centrifugation is performed at about 500-1000 g for 5-20 min. In some embodiments, the first centrifugation is performed at about 500-900 g for about 5-15 min. In some embodiments, the second centrifugation is performed at about 1000-3000 g for 5-30 min. In some embodiments, the second centrifugation is performed at about 1500-2500 g for 5-20 min.

In some embodiments, the second centrifugation is performed at about 1500-2200 g for about 5-15 min. In some embodiments, the third centrifugation is performed at about 10000-30000 g for 15-60 min. In some embodiments, the third centrifugation is performed at about 12000-25000 g for 20-60 min. In some embodiments, the third centrifugation is performed at about 12000-20000 g for 20-40 min. In some embodiments, the fourth centrifugation is performed at about 10000-30000 g for 15-60 min. In some embodiments, the fourth centrifugation is performed at about 12000-25000 g for 20-60 min. In some embodiments, the fourth centrifugation is performed at about 12000-20000 g for 20-40 min.

In some embodiments, a vesicle bearing specific markers may be enriched by enrichment methods for specific markers. After sufficient vesicles are obtained, the culture medium is collected, and a specific vesicle is purified and separated from the culture medium. This may be achieved by any suitable method known in the art. Such methods include, for example, original methods of separating exosomes by differential ultracentrifugation, as well as more recent methods such as polymer precipitation (ExoQuick™ from SBI, Palo Alto, CA), immunoaffinity capture (Greening et al. 2015, *Methods in Molecular Biology*), immunomagnetic capture (exo-FLOW™, SBI) and the like.

Immunoaffinity purification is a method for selective capture of a specific vesicle based on surface markers. The efficient capture of a vesicle is achieved by high affinity coupling between streptavidin covalently coated magnetic beads and biotinylated capture antibodies. The captured vesicle, after elution, is structurally intact and biologically active. Based on the discovery of the present disclosure that the vesicle specifically express Annexin V, Flotillin-1, Cadherin 11, Integrin alpha 5, and Syntaxin 4 molecules at high levels, the method may be used in the present disclosure separate or purify or enrich the vesicle.

In some embodiments, the vesicle can also be enriched by a method of immunomagnetic beads, wherein the immunomagnetic beads are obtained by coupling an antibody to magnetic beads; the monoclonal antibody further includes one or more of an anti-Annexin V antibody, an anti-Flotillin-1 antibody, an anti-Cadherin 11 antibody, and an anti-Integrin alpha 5 antibody.

In some embodiments, the present disclosure further provides an induced vesicle derived from IPS cells. It is a subcellular product produced by intervening or inducing apoptosis of IPS cells when the IPS cells are normally viable.

When the term "enrich" is used in this application, it covers the separation of one or more vesicles from any other vesicles present in a sample or it means that a vesicle present in a composition including the vesicle with a content of a higher total percentage than when it is found to be present in a tissue of an organism.

In an embodiment, the enriched vesicle is not separated from the sample, but is subjected to any diagnosis while it is still present in the sample. The sample may then be presented on a slide, and may be diagnosed using a microscope, and in this embodiment, the vesicle is detected without being separated.

In another embodiment, the enriched vesicle is separated from the sample.

Immunomagnetic bead-based separation (IMS) is a new immunological technique developed in recent years. Immunomagnetic beads (IMB) can not only bind to active protein antibodies, but also can be attracted by magnets. After processing, an antibody may be bound to the magnetic beads such that the magnetic beads serve as a carrier of the antibody. After the antibody on the magnetic beads binds to a specific antigen, an antigen-antibody-magnetic bead immune complex is formed, and such complex mechanically moves under the action of magnetic force, so that the complex is separated from other substances, thus achieving the purpose of separating the specific antigen. Immunomagnetic beads (IMB) provide a platform which can be applied in all fields utilizing the principle of antigen-antibody binding, and its use has achieved remarkable results in the fields of medicine and biology for, such as, bone marrow transplantation, separation of stem cells, organelles, cancer cells, hormones, pathogens and toxins, etc. In recent years, IMB has been widely used in the separation and detection of mycotoxins in foods, water, biological samples and environmental samples due to its high sensitivity and specificity, showing good development and application prospects.

The method of immunomagnetic beads described in the present disclosure is a method in which magnetic beads, which are bound to a specific antibody, bind to a target vesicle with a specific surface antigen, and then are absorbed by a magnetic field adsorption for extraction of the target vesicle.

In some embodiments of the present disclosure, the vesicle is enriched specifically by adding immunomagnetic beads coated with one or more antibodies of an anti-Syntaxin 4 antibody, an anti-Annexin V antibody, an anti-Flotillin-1 antibody, an anti-Cadherin 11 antibody, and an anti-Integrin alpha 5 antibody to the cell culture supernatant containing the vesicle. In this way, the vesicle which specifically binds to one or more antibodies of the anti-Syntaxin 4 antibody, the anti-Annexin V antibody, the anti-Flotillin-1 antibody, the anti-Cadherin 11 antibody, and the anti-Integrin alpha 5 antibody can be separated, and the purpose of enriching a specific vesicle can be achieved. In some preferred embodiments, when immunomagnetic beads coated with all of the anti-Syntaxin 4 antibody, the anti-Annexin V antibody, the anti-Flotillin-1 antibody, the anti-Cadherin 11 antibody, and the anti-Integrin alpha 5 antibody are used to separate a vesicle, the vesicle can be separated with the highest purity, and enables the most effective treatment for diseases such as hemophilia A.

In some preferred embodiments, optimization is made by a combined method in which centrifugation is firstly performed to efficiently remove impurities such as cells and cell debris in the cell culture supernatant, and then immunomagnetic beads coated with one or more antibodies of an anti-Syntaxin 4 antibody, an anti-Annexin V antibody, an anti-Flotillin-1 antibody, an anti-Cadherin 11 antibody, and an anti-Integrin alpha 5 antibody are added to the cell culture supernatant containing the vesicle. In this way, the vesicle which specifically binds to the antibodies can be separated, and the purpose of enriching a specific vesicle can be achieved.

In some embodiments, the mesenchymal stem cells are derived from a human or a mouse, but are not limited thereto.

In some embodiments, the mesenchymal stem cells include, but are not limited to, bone marrow-derived mesenchymal stem cells, urine-derived mesenchymal stem cells, oral cavity-derived mesenchymal stem cells, adipose-derived mesenchymal stem cells, placenta-derived mesenchymal stem cells, umbilical cord-derived mesenchymal stem cells, periosteum-derived stem cells, or a combination thereof.

In some embodiments, the mesenchymal stem cells are selected from the group consisting of bone marrow-derived mesenchymal stem cells, adipose-derived mesenchymal stem cells, umbilical cord-derived mesenchymal stem cells, and oral cavity-derived mesenchymal stem cells.

BRIEF DESCRIPTION OF THE DRAWINGS

FIG. 4A shows particle diameter distribution of flow cytometry of IEVs; FIG. 4B shows the scattered light intensity of side scatter (SSC) analysis of IEVs, indicating the particle diameter distribution of the IEVs; FIG. 4C shows the scattered light intensity of IEVs analyzed by standardized small particle microspheres produced by Bangs Laboratories, indicating the particle diameter distribution of IEVs; FIG. 4D shows IEVs observed by transmission electron microscopy (TEM), indicating the particle diameter distribution of IEVs; FIG. 4E shows Nanoparticle Tracking Analysis (NTA), indicating the particle diameter distribution of IEVs; and FIG. 4F shows particle size measurements of IEVs at the single-vesicle level using a nano-flow cytometry technique, indicating the particle diameter distribution of IEVs.

FIG. 6A shows the results of proteomic quantitative analysis of MSCs, MSCs-exosomes and MSCs-IEVs by the DIA quantitative technique; FIG. 6B shows a heat map drawn by screening for IEVs-specific highly expressed proteins; FIG. 6C shows the results of GO enrichment analysis of differential proteins, indicating the expressions of Annexin V, Flotillin-1, Cadherin 11, Integrin alpha 5, and Syntaxin 4 molecules in IEVs; and FIG. 6D shows the results of Western Blot verification of the expressions of Annexin V, Flotillin-1, Cadherin 11, Integrin alpha 5, and Syntaxin 4, in MSCs, MSCs-exosomes, and MSCs-IEVs.

FIG. 8A shows the change in the coagulation factor VIII; FIG. 8B shows the change in the vWF factor. FIG. 8C shows the change in the tissue factor (TF); FIG. 8D shows the change in prothrombin.

Note: WT is a wild-type mouse; HA group is a hemophilia A mice model; HA+IEVs is a hemophilia A mice model administered with IEVs treatment; HA+PS-IEVs is a hemophilia A mouse model administered with PS-negative IEVs; HA+TF-IEVs is a hemophilia A mouse model administered with TF-negative IEVs; and HA+Exosomes is a hemophilia A mouse model administered with exosomes.

Figure 11:
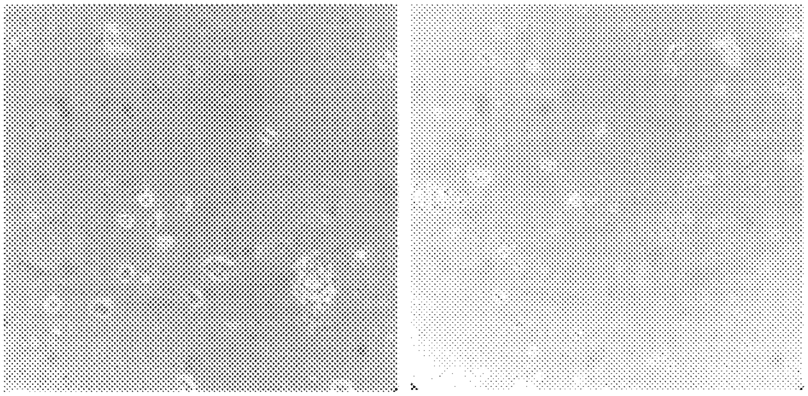

FIG. 11 shows morphologies of MC3T3-E1 and hBMMSCs-derived IEVs.

Figure 12:
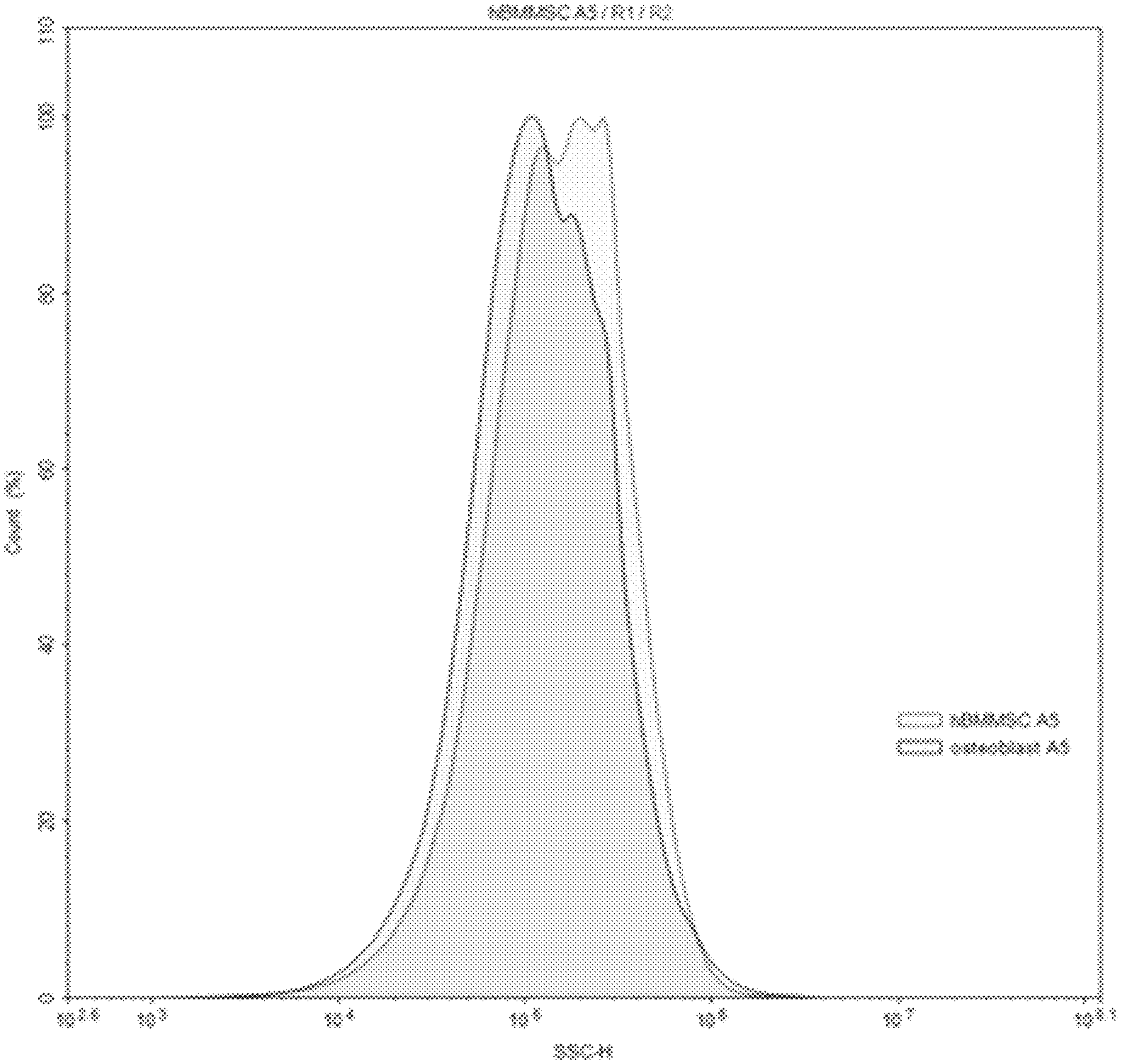

FIG. 12 shows the results of flow cytometry of particle diameter distribution of MC3T3-E1 and hBMMSCs-derived IEVs.

Figure 13A:
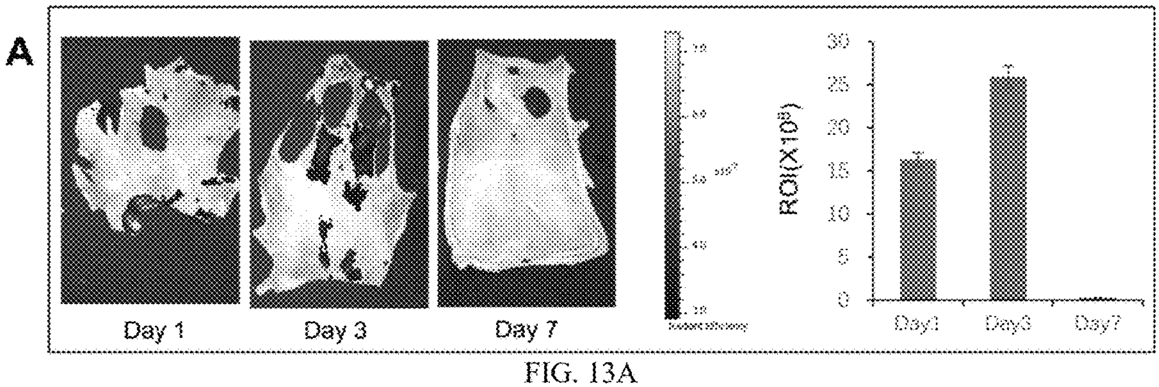
Figure 13B:
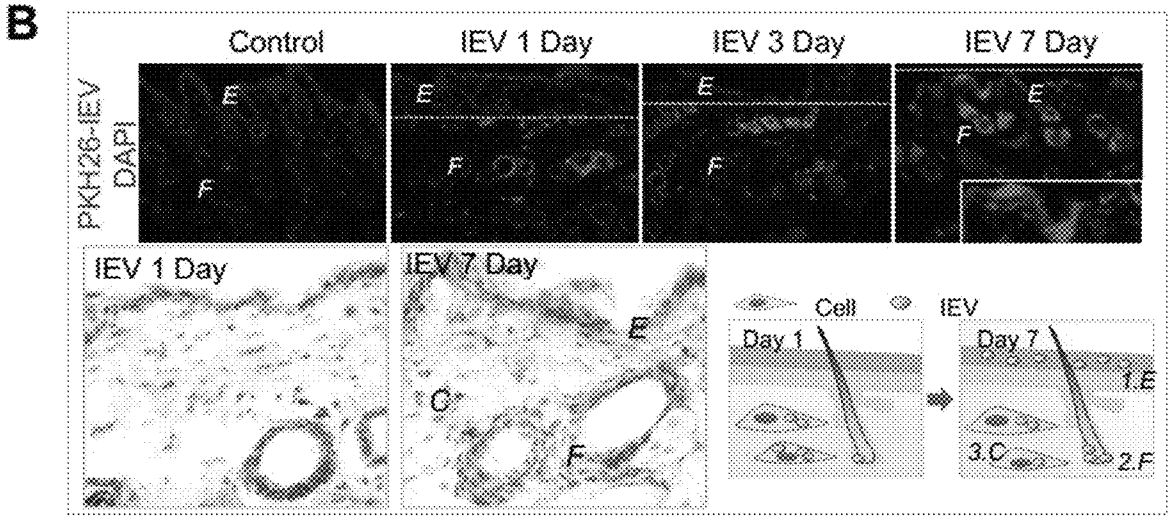
Figure 13C:
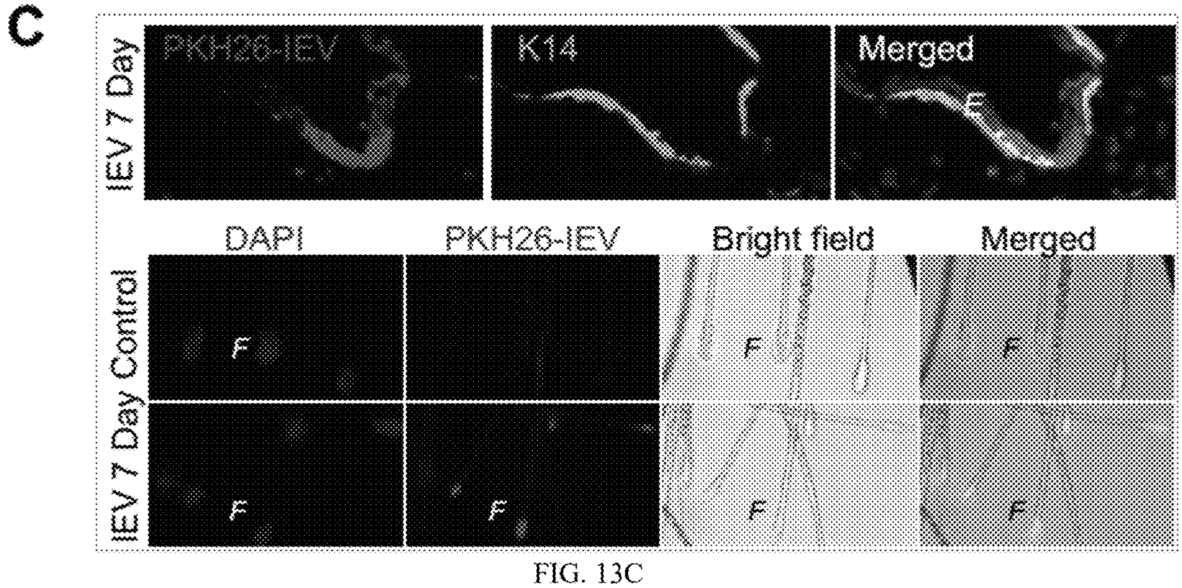

FIGS. 13A-13C show that the excretion of IEVs through the skin and hair: FIG. 13A shows the dynamic metabolism of IEVs at the skin surface. FIG. 13B shows the gradual migration of IEVs from the subcutaneous tissue to the dermis and epidermis over time. FIG. 13C shows the presence of PKH26-IEVs in hair follicles found in hairs removed from the surface of mice on Day 7.

Figure 14:
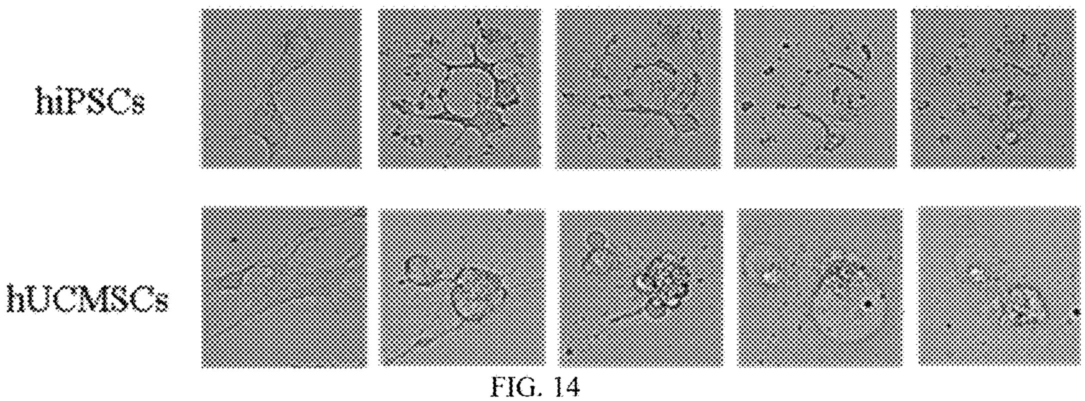

FIG. 14 shows the death processes of hiPSCs and hUCMSCs taken by a High Content Cellular Imaging Analysis System.

Figure 15:
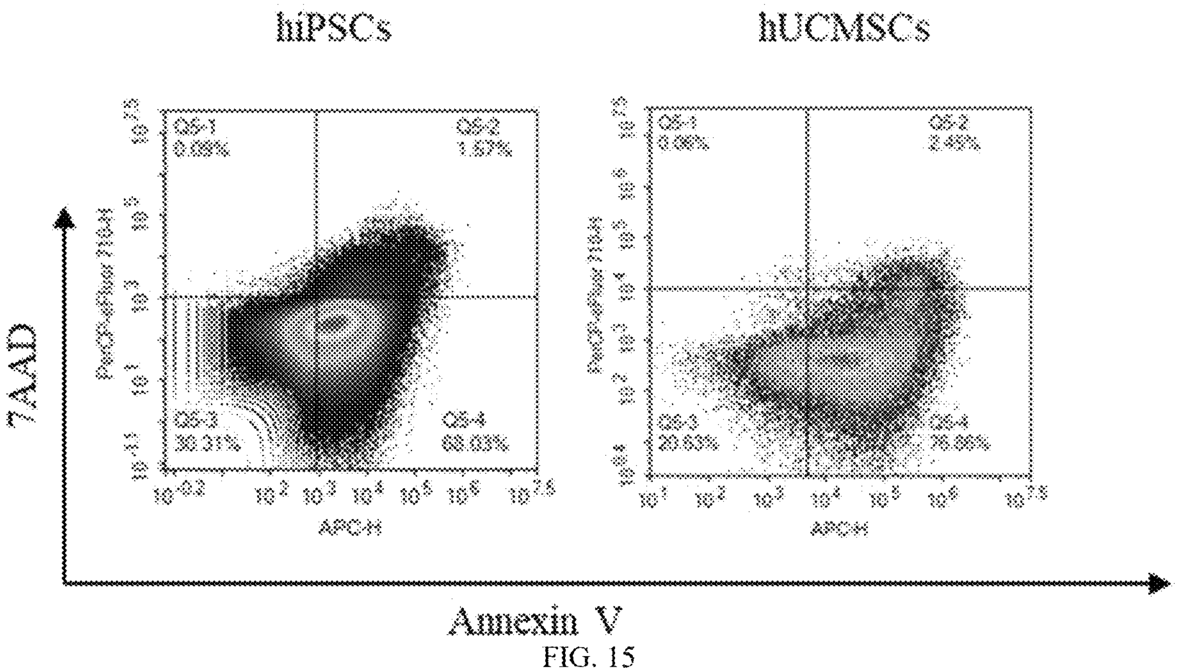

FIG. 15 shows the apoptosis rates of hiPSCs and hUCMSCs induced to apoptosis analyzed by flow cytometry, demonstrating that most cells underwent apoptosis.

Figure 16:
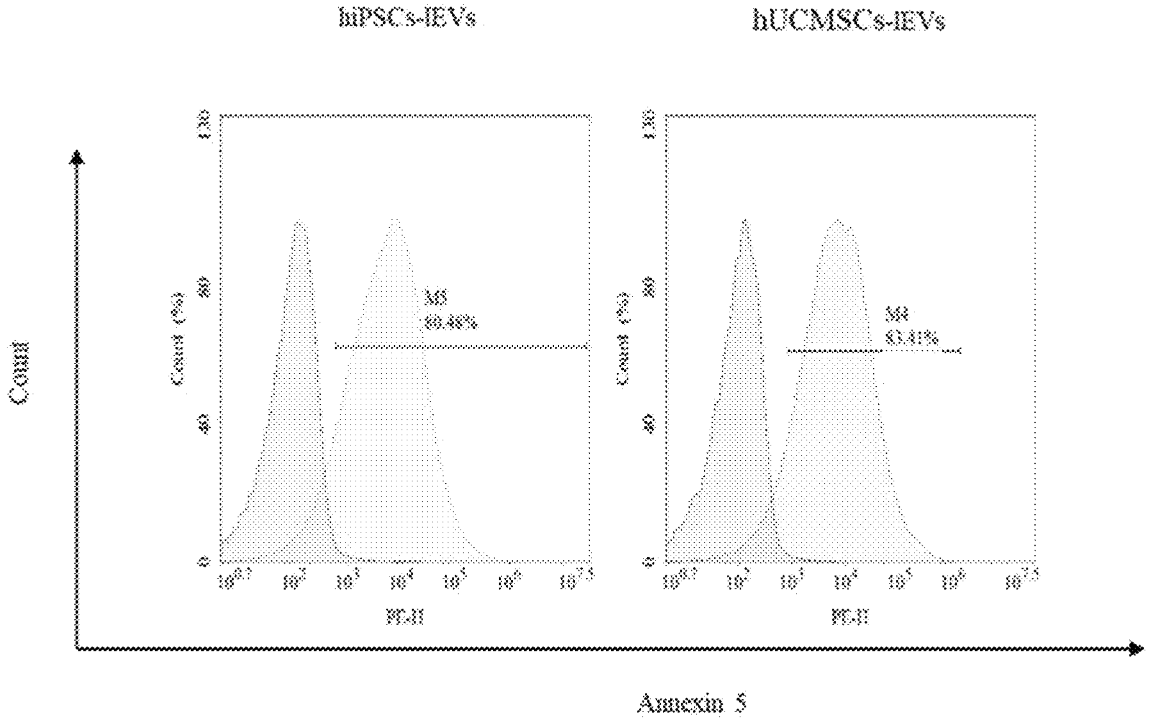

FIG. 16 shows that the positive rates of Annexin 5 expression by flow cytometry were over 80% for both hiPSCs and hUCMSCs.

Figure 17:
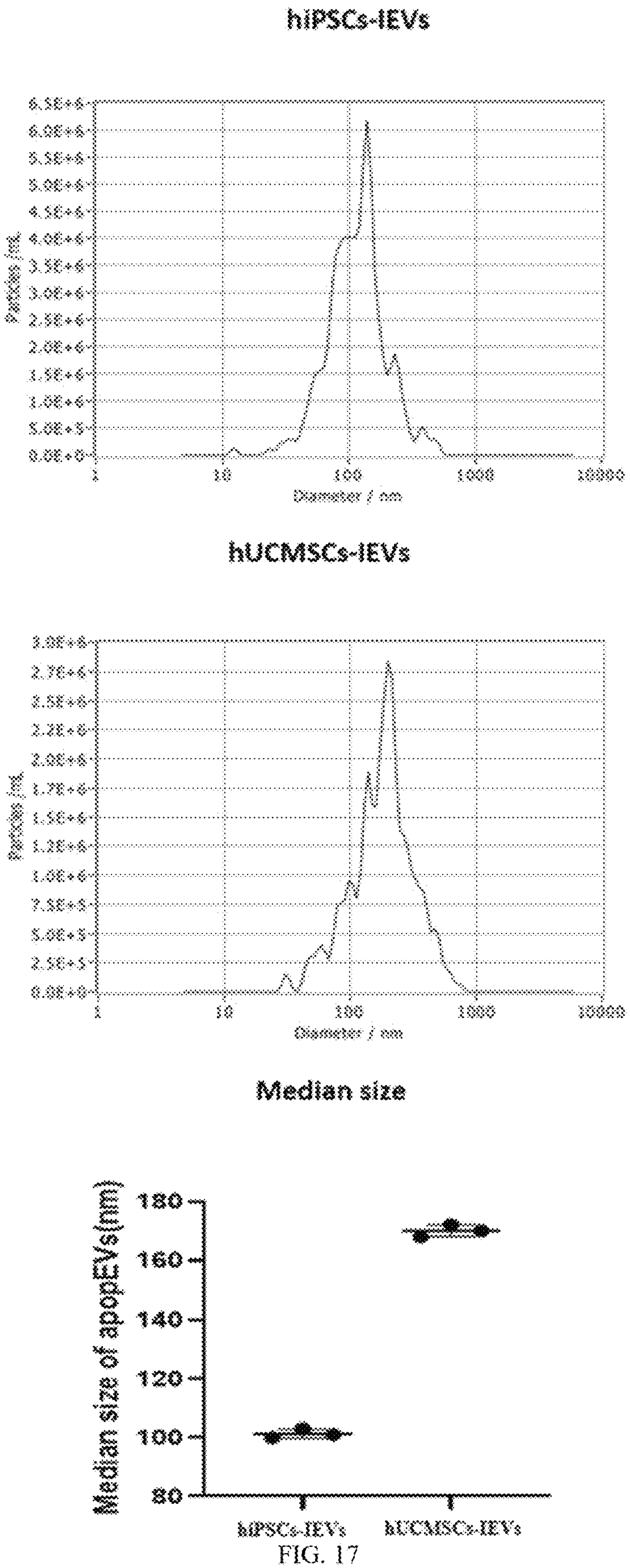

FIG. 17 shows the particle sizes of two IEVs as measured by nanoparticle tracking analysis (NTA).

Figure 18:
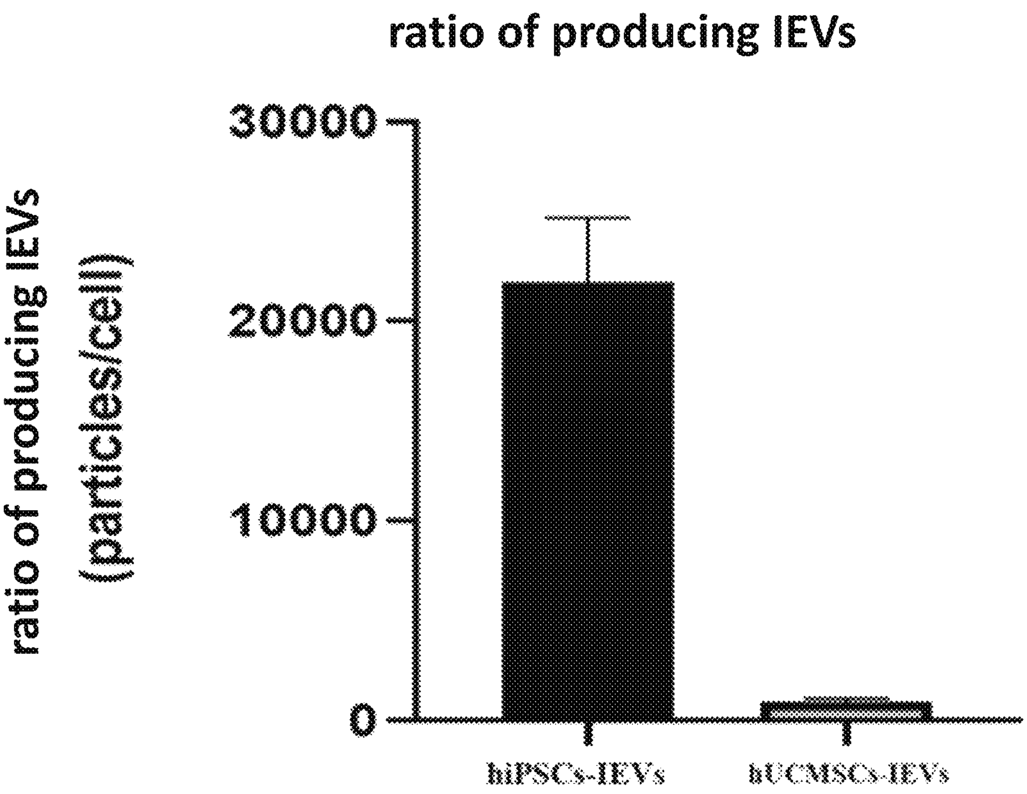

FIG. 18 shows the amount of IEVs produced by the two IEVs measured by nanoparticle tracking analysis (NTA).

Figure 19:
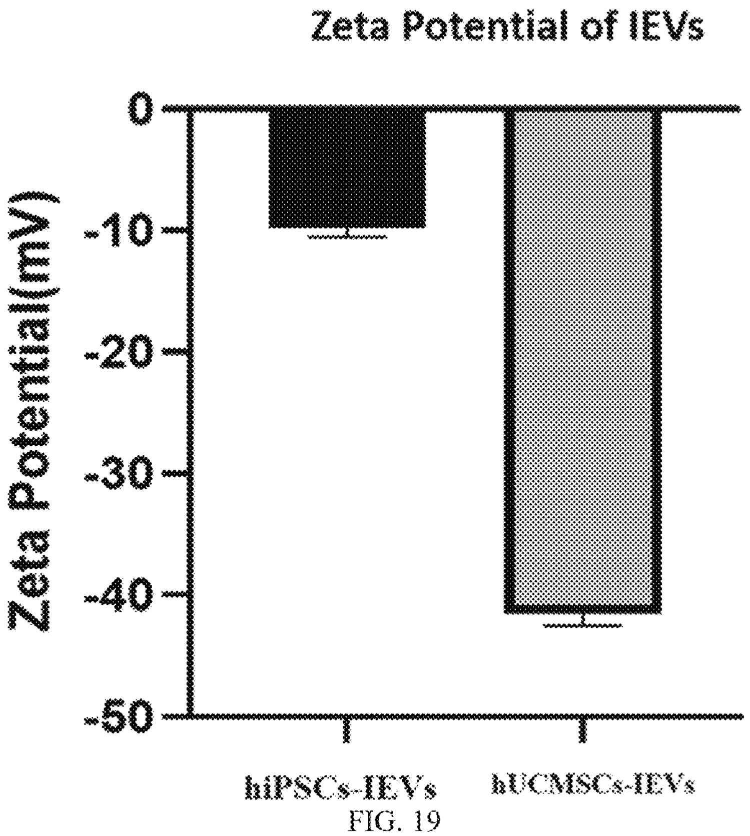

FIG. 19 shows the potentials of two IEVs as measured by nanoparticle tracking analysis (NTA).

DETAILED DESCRIPTION

The embodiments of the present disclosure are further illustrated by the following specific examples, which are not intended to limit the scope of the disclosure. Certain insubstantial modifications and adaptations made by others in light of the disclosed concepts remain within the scope of the disclosure.

The IEVs in the examples of the present disclosure is an abbreviation for induced vesicles, and induced extracellular vesicles (IEVs). An induced extracellular vesicle refers to a subcellular product that is produced by intervening or inducing apoptosis of precursor cells (e.g. stem cells) which are normally viable. Such subcellular product generally has a membrane structure, expresses apoptotic markers, and partially contains the genetic material DNA. The inventors have found that the induced extracellular vesicle is a substance that distinguishes between cells and conventional extracellular vesicles (e.g. exosomes, etc.). In some embodiments, normal viable cells are, for example, non-apoptotic cells, non-senescent cells, non-senescent cells with arrested proliferation, non-post-cryopreservation cells, non-malignant cells with abnormal proliferation, or non-damaged cells, etc. In some embodiments, the normally viable cells are taken from cells at 80-100% confluence in the cell culture process. In some embodiments, the normally viable cells are taken from cells in the log phase. In some embodiments, the normally viable cells are taken from primary culture cells derived from a human or murine tissues and subculture cells thereof. In some embodiments, the normally viable cells are taken from an established cell line or cell strain. In some embodiments, the precursor cells are taken from early cells.

In the present disclosure, IEV is equivalent to IEVs. In the present disclosure, STS refers to staurosporine. In the present disclosure, exosomes refer to exosomes.

“Including” or “comprising” is intended to mean that the compositions (e.g. media) and methods include the recited elements, but not excluding others. When used to define compositions and methods, “consisting essentially of” means excluding other elements of any significance to the combination for the stated purpose. Thus, a composition substantially consisting of the elements defined herein does not exclude other materials or steps that do not substantially affect the basic and novel features of the claimed disclosure. “Consisting of” means excluding trace elements of other components and substantial method steps. Embodiments defined by each of these transition terms are within the scope of this disclosure.

An “effective amount” is an amount sufficient to achieve a beneficial or desired result, e.g., an enhanced immune response, treatment, prevention, or amelioration of a medical condition (disease, infection, etc.), and so on. An effective amount may be applied in one or more administrations, applications or dosages. The appropriate dosage will vary depending on the body weight, age, health, the disease or condition to be treated, and the way of administration.

As used herein, the terms “high expression” and the like are intended to include increased expression of nucleic acids or proteins to levels higher than those contained in prior art vesicles (e.g. exosomes).

As used herein, the term "pharmaceutically acceptable carrier" refers to any of standard pharmaceutical carriers, such as lyophilized powders, injections, tablets, capsules, kits, or patches. Typically such carriers contain excipients such as starch, milk, sugar, certain types of clays, gelatin, stearic acid or salts thereof, magnesium or calcium stearate, talc, vegetable fats or oils, gums, glycols, or other known excipients. Such carriers may also include flavoring and color additives, or other ingredients. Examples of pharmaceutically acceptable carriers include, but are not limited to, the following: water, saline, buffers, and inert non-toxic solids (e.g. mannitol and talc). Compositions including such carriers are formulated by well-known conventional methods. Depending on the intended mode of administration and intended use, the compositions may be in the form of solid, semi-solid or liquid dosage forms, such as powders, granules, crystals, liquids, suspensions, liposomes, pastes, creams, ointments, and the like, and may be in unit dosage forms suitable for administration of relatively precise dosages.

In the present disclosure, the components of the "composition" may be present in admixture or may be packaged separately. Separately packaged components may also contain their respective adjuvants. The adjuvant refers to a means used in pharmacy to aid the therapeutic efficacy of a drug. Where the components of the composition are packaged separately, the separately packaged components may be administered simultaneously or sequentially in any order where the patient is first treated with one drug and then administered with another drug. The patient refers to a mammalian subject, particularly a human subject.

In the present disclosure, the "composition" may also be present such that one component is encapsulated by another component. In some embodiments, in the composition, the induced vesicle serves as a drug carrier, and a drug for treating or preventing a disease is encapsulated in the induced vesicle.

In the present disclosure, the sources of corresponding reagents are as follows: Penicillin/Streptomycin Solution (BIOSOURCE; P303-100); Glutamine (BIOSOURCE; P300-100); Dexamethasone Sodium Phosphate (Sigma; D-8893); α-MEM (Gibco; 12571-063); 2-ME (GIBCO; 21985-023).

Example 1 Separated Culture of MSCs

In accordance with the guidance of the Animal Ethics Committee, mice were sacrificed with excess $CO_2$. Under sterile conditions, the tibia and femur were removed, and the attached muscle and connective tissue were stripped out. Then the metaphysis was further separated to expose the bone marrow cavity. PBS containing 10% by volume of fetal bovine serum was drawn using a 10 mL sterile syringe to repeatedly flush the bone marrow cavity, and was filtered with a 70 μm pore cell strainer, and centrifuged at 500 g for 5 min. After the supernatant was removed, the cell pellet at the bottom was collected, and then resuspend in PBS and centrifuged at 500 g for 5 min again to collect the final cell pellet. The cells were then subjected to flow cytometry sorting with CD34− and CD90+ as sorting criteria, such that BMMSCs were separated. Finally, the cells were resuspended in a Dex (−) culture solution, and inoculated to a 10 cm diameter cell culture dish and cultured at 37° C. in 5% $CO_2$. After 24 h, non-adherent cells in the supernatant were removed by aspiration, washed with PBS, and added into the Dex (−) culture solution for further culture. After 1 week, an equal amount of Dex (+) culture solution was added, and after another week, dense primary BMMSCs colonies were observed. The BMMSCs were digested by trypsin incubation at 37° C., and passaged for amplification. Thereafter, the Dex (+) culture solution was changed every 3 days, and subcultured if confluent. The BMMSCs of second passage (P2) were taken for subsequent experiments.

The composition of the Dex (−) culture solution is shown in Table 1, and the composition of Dex (+) culture solution is shown in Table 2:

TABLE 1

Formulation Table of Dex (−) Culture Solution

| reagents | volume | final concentration |
|---|---|---|
| FBS | 100 mL | 20% |
| penicillin/streptomycin solution (10,000 U/mL) | 5 mL | 100 U/mL |
| glutamine (200 mM) | 5 mL | 2 mM |
| 2-ME (55 mM) | 500 μL | 55 μM |
| α-MEM | | add to 500 mL |

TABLE 2

Formulation Table of Dex (+) Culture Solution

| reagents | volume | final concentration |
|---|---|---|
| FBS | 100 mL | 20% |
| penicillin/streptomycin solution (10,000 U/mL) | 5 mL | 100 U/mL |
| glutamine (200 mM) | 5 mL | 2 mM |
| Dexamethasone Sodium Phosphate ($10^{-4}$M) | 50 μL | $10^{-8}$M |
| 2-ME (55 mM) | 500 μL | 55 μM |
| α-MEM | | add to 500 mL |

The purity of the separated BMMSCs was assessed by flow cytometry analysis of surface markers. For surface marker identification, P2 BMMSCs were harvested by trypsinization, and then washed once with PBS containing 3% FBS to be resuspended in the PBS at a density of $5\times10^5$/mL. Then, 1 μL of PE fluorescent conjugated CD29, CD44, CD90, CD45, and CD34 antibodies were added, with the blank group left. Incubation was carried out for 30 min in the dark at 4° C., followed by washing with PBS for 2 times, and then tests were carried out on the instrument. The results of flow cytometry are shown in FIGS. 1A-1E. It can be seen that the separated cells are BMMSCs (bone marrow mesenchymal stem cells).

Example 2 Obtaining of Induced Vesicle

The MSCs cultured to the second passage in Example 1 (bone marrow-derived MSCs, BMMSCs) was further cultured with the medium (Dex (+) culture solution) in Example 1 until the cells were 80%-90% confluent, then washed twice with PBS, added with a serum-free medium (α-MEM medium) containing 500 nM STS to induce apoptosis, and incubated at 37° C. for 24 h, and the cell supernatant was collected for separation and extraction of IEVs.

Figure 1A:
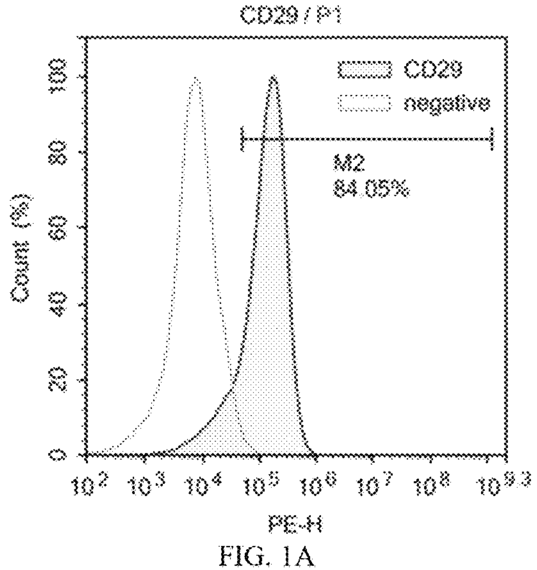
FIGS. 1A-1E show the results of flow cytometry of surface markers of separated BMMSCs.
Figure 1B:
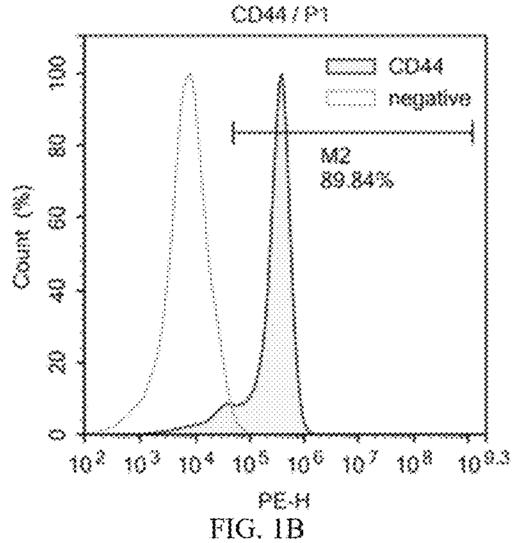
Figure 1C:
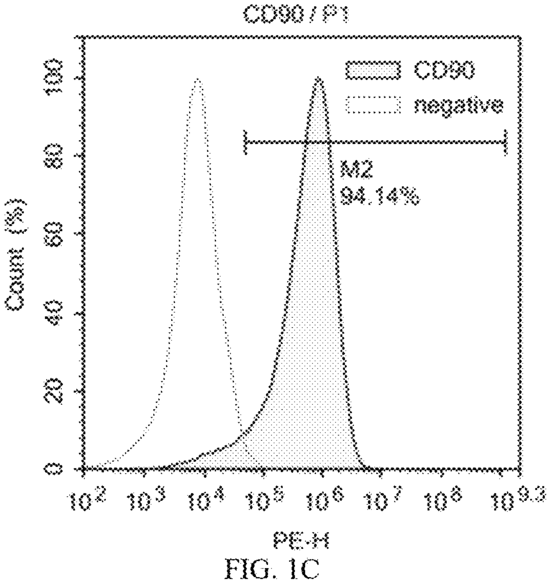
Figure 1D:
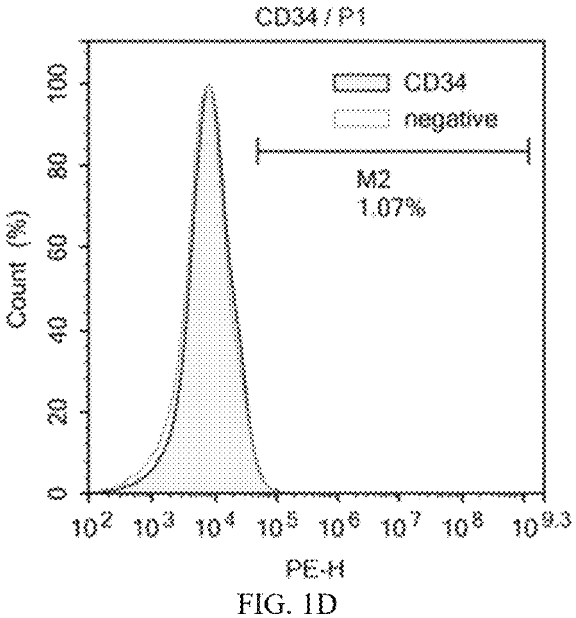
Figure 1E:
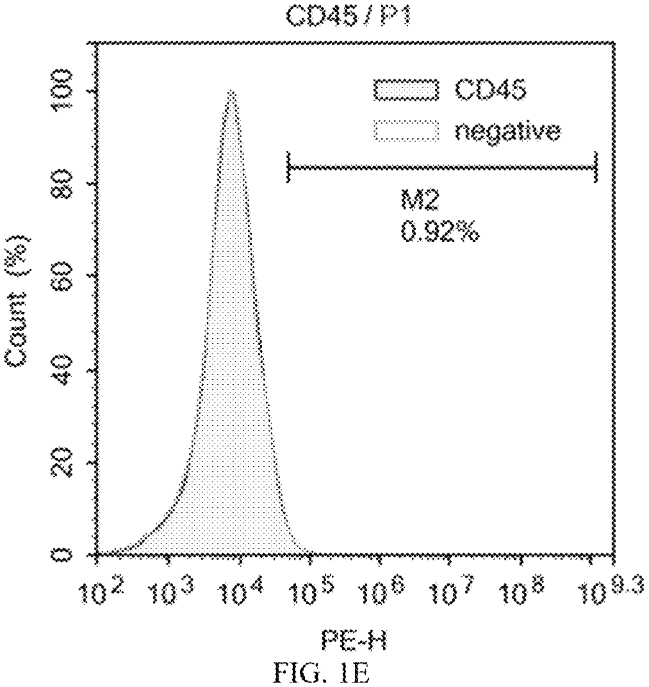
Figure 2:
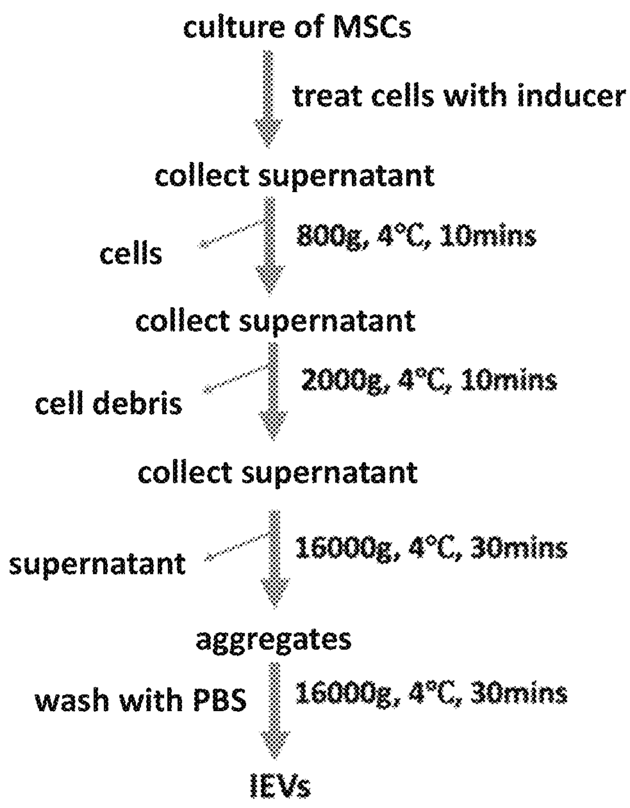
FIG. 2 shows an operation flow chart of Example 2.

The IEVs were separated and extracted from the collected cell supernatant. The operation process is shown in FIG. 2, specifically includes the steps of: performing centrifugation at 800 g for 10 min and collecting the supernatant; then performing centrifugation at 2000 g for 10 min and collecting the supernatant; then performing centrifugation at 16000 g for 30 min, removing the supernatant, and resuspending the IEVs in a sterile PBS; then performing centrifugation at 16000 g for 30 min, removing the supernatant, and resuspending the IEVs in 300-500 μL of sterile PBS.

Comparative Example 1 Separation and Extraction of Exosomes from the Same MSCs Source The MSCs cultured to the second passage in Example 1 (bone marrow-derived MSCs, BMMSCs) was further cultured with the medium in Example 1 until the cells were 80%-90% confluent, then washed twice with PBS, added with a serum-free medium, and incubated at 37° C. for 48 h, and the cell supernatant was collected for separation and extraction of exosomes.

The extraction steps include: centrifuging at 800 g for 10 min—collecting supernatant—centrifuging at 2000 g for 10 min—collecting supernatant—centrifuging at 16000 g for 30 min—collecting supernatant—centrifuging at 120000 g for 90 min—removing supernatant and resuspending pellet in sterile PBS—centrifuging again at 120000 g for 90 min, removing supernatant, collecting bottom exosomes, and resuspending in sterile PBS.

Example 3 Analysis of IEVs

1. Quantitative and Membrane Protein Analysis of IEVs

Figure 3:
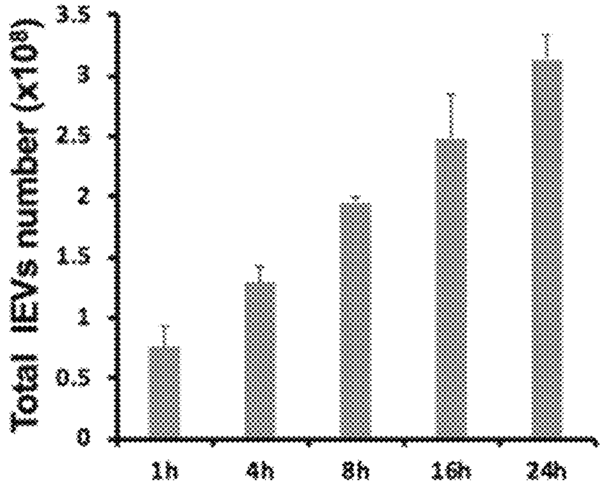
FIG. 3 shows the statistics on the count of IEVs produced by MSCs ($10^6$ MSCs) analyzed by flow cytometry.

The quantitative analysis of IEVs obtained in Example 2 was performed using flow cytometry, and the time points for measurement were 1 h, 4 h, 8 h, 16 h and 24 h. The results showed that $10^6$ MSCs could produce $0.76\times10^8$, $1.29\times10^8$, $1.95\times10^8$, $2.48\times10^8$ and $3.14\times10^8$ IEVs after induction to 1 h, 4 h, 8 h, 16 h and 24 h, respectively. It can be seen that a single MSC could produce 300 IEVs after induction to 24 h (FIG. 3).

Figure 4A:
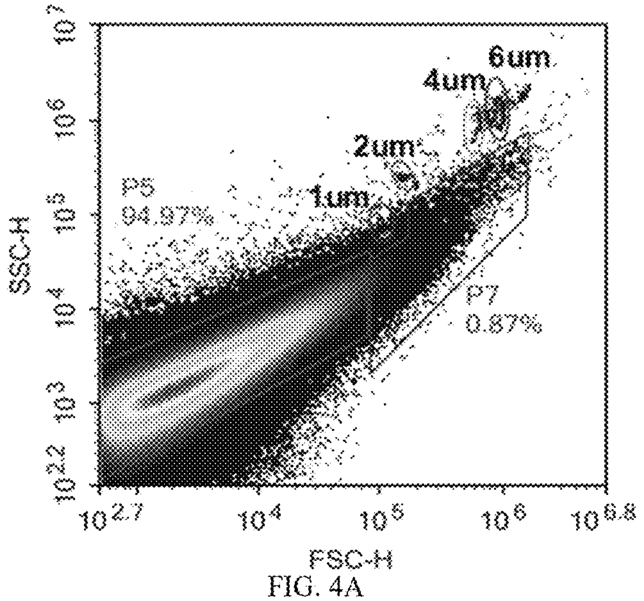
FIG. 4A-4F show diameter measurements of IEVs particles.
Figure 4B:
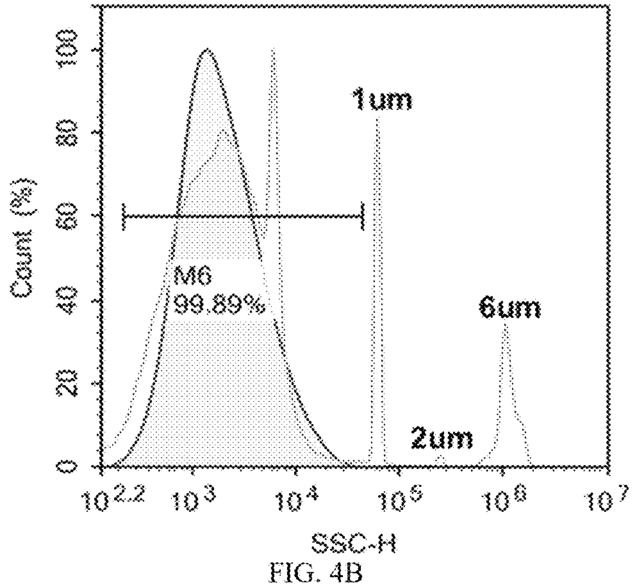
Figure 4C:
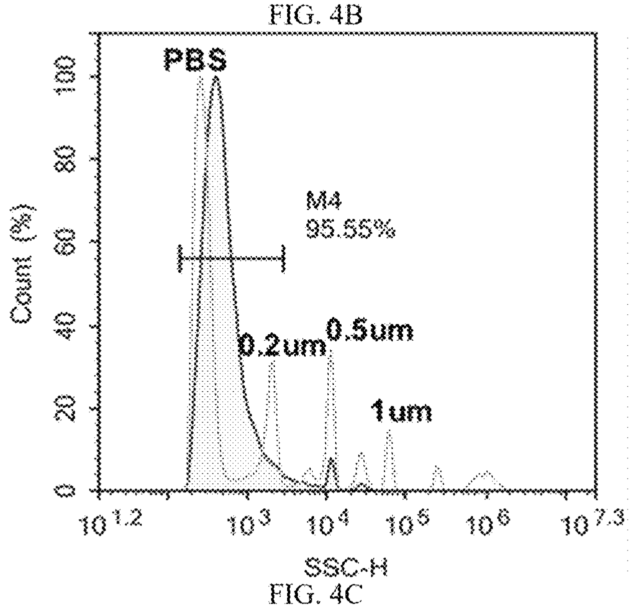
Figure 4D:
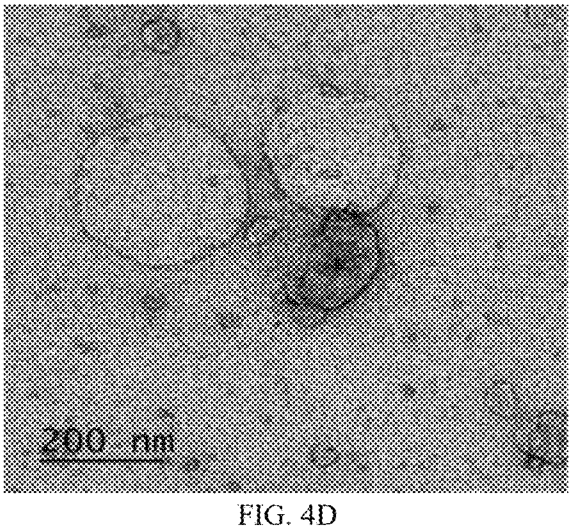
Figure 4E:
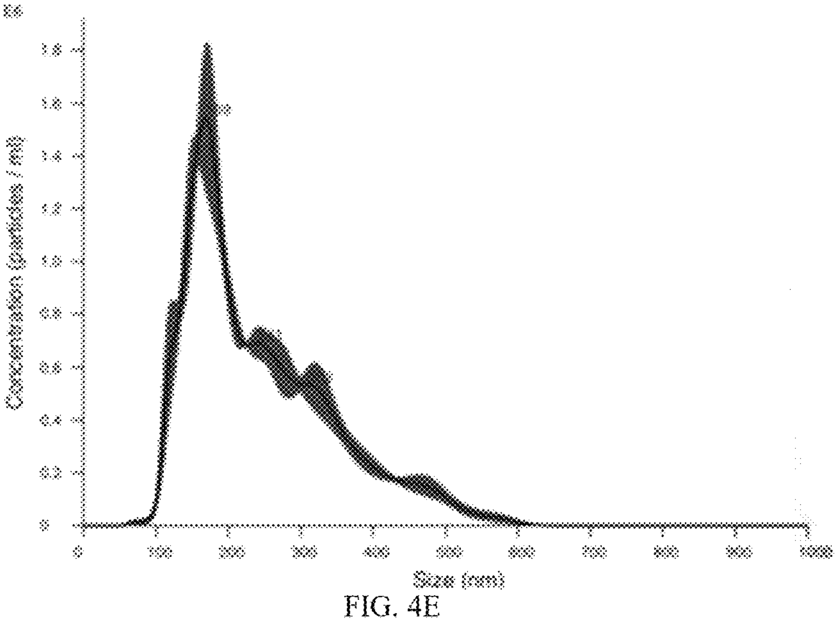
Figure 4F:
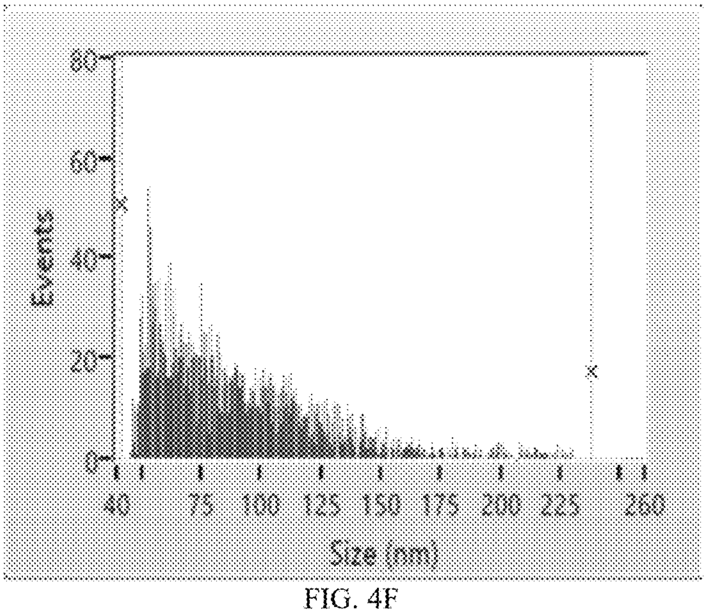
Figure 5A:
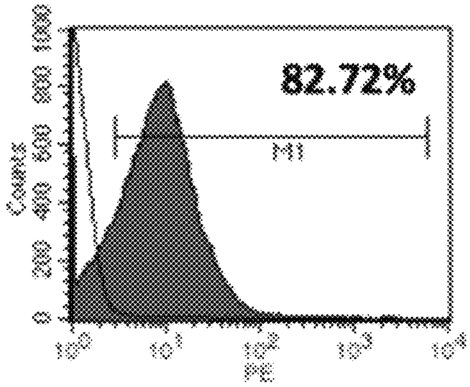
FIGS. 5A-5K show the results of surface membrane protein analysis of IEVs by flow cytometry.
Figure 5B:
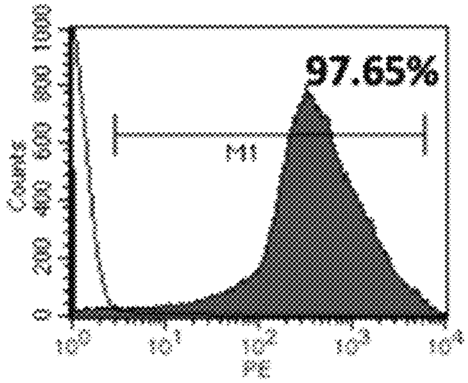
Figure 5C:
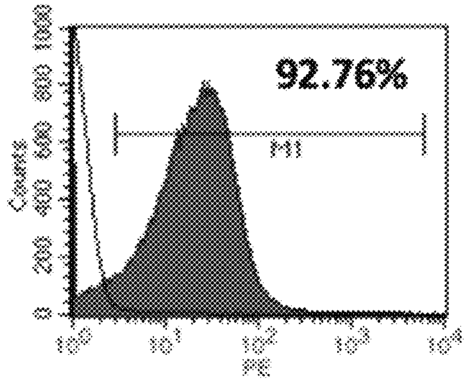
Figure 5D:
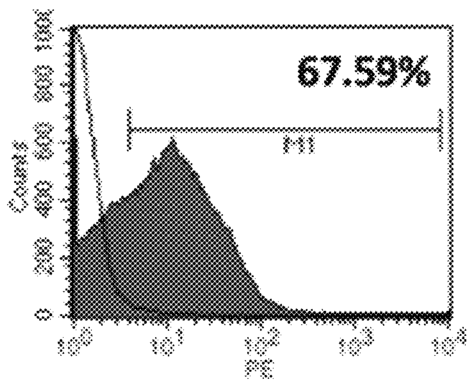
Figure 5E:
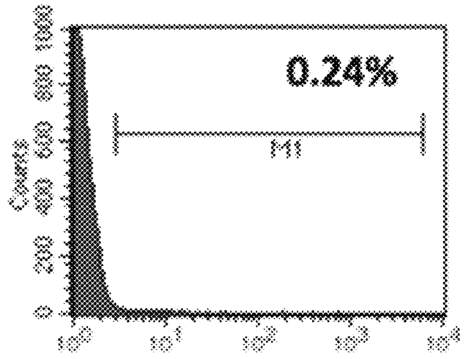
Figure 5F:
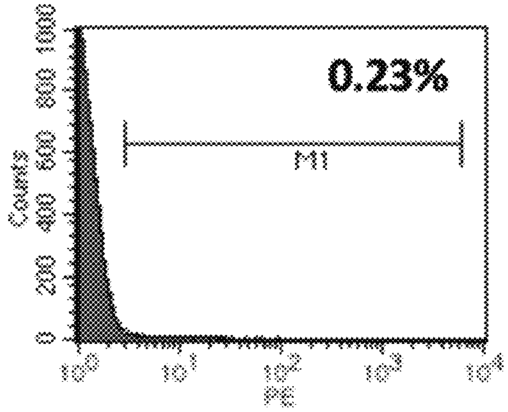
Figure 5G:
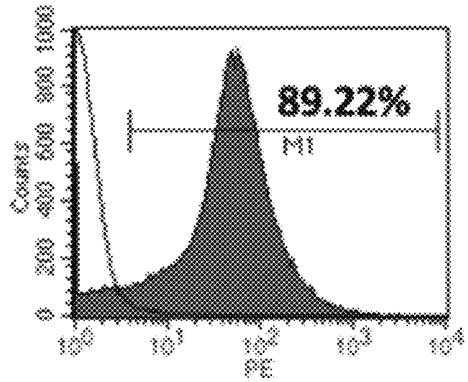
Figure 5H:
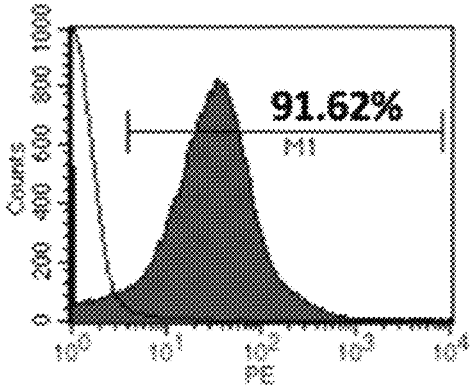
Figure 5I:
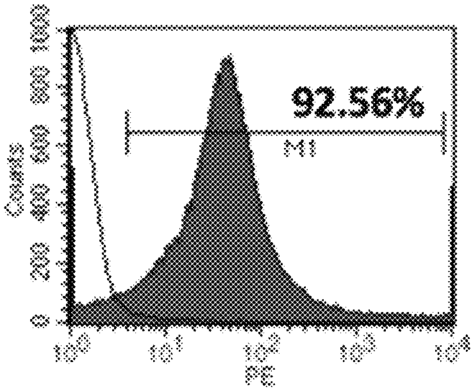
Figure 5J:
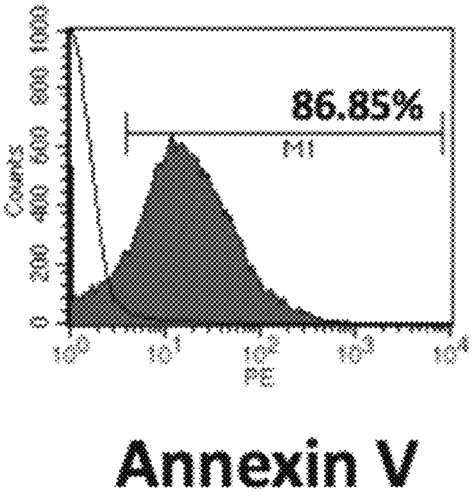
Figure 5K:
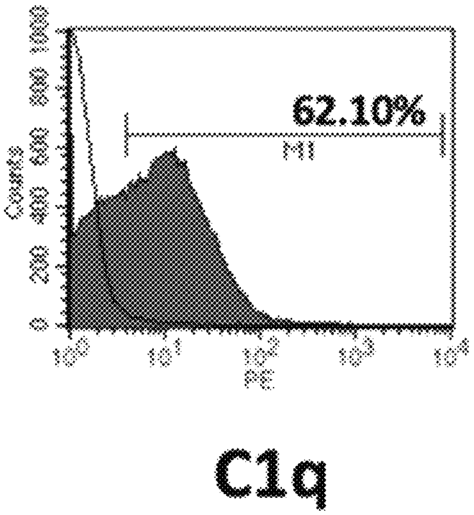

In addition, the particle diameter distribution of IEVs found by flow cytometry was concentrated within less than 1 μm, accounting for 94.97% (FIG. 4A). The results of side scatter (SSC) analysis also showed that the scattered light intensity of IEVs was concentrated in the range of less than 1 μm (FIG. 4B). Further, the scattered light intensity of IEVs was analyzed by standardized small particle microspheres (0.2 μm, 0.5 μm, and 1 μm) produced by Bangs Laboratories, and the results showed that the particle diameters of IEVs were all below 0.2 μm (FIG. 4C). Transmission electron microscopy (TEM) showed similar results as flow cytometry, with most vesicles at and below 200 nm in diameter (FIG. 4D). Nanoparticle tracking analysis (NTA) was consistent with TEM observations, with IEVs particles averaging 169 nm in diameter (FIG. 4E). Particle size measurements at the single-vesicle level using a state-of-the-art nano-flow cytometry technology also showed that the average particle diameter of IEVs was at 100.63 nm (FIG. 4F).

The surface membrane proteins of the IEVs extracted in Example 2 were analyzed by flow cytometry, and the results showed that the IEVs derived from MSCs expressed surface proteins similar to MSCs, i.e., CD29, CD44, CD73, CD166 positive, and CD34, CD45 negative. At the same time, IEVs could express the ubiquitous surface proteins CD9, CD63, CD81 and C1q of extracellular vesicles (FIG. 5A-5K).

2. Content Analysis for IEVs

Figure 6A:
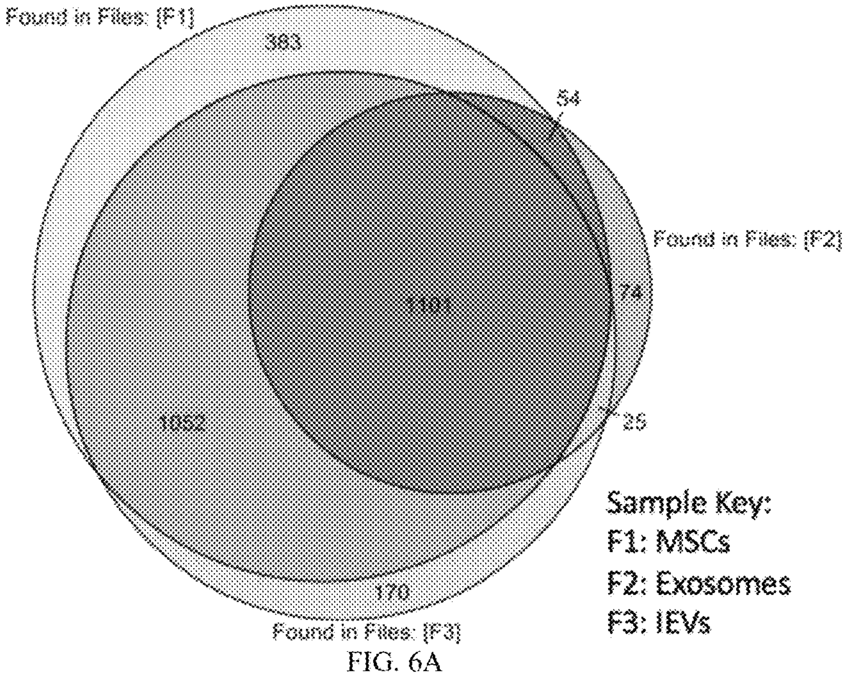
FIGS. 6A-6D show the content analysis of IEVs.

Proteomic quantification of BMMSCs, MSCs-exosomes (extracted in Comparative Example 1), and MSCs-IEVs (obtained in Example 2) was performed using the protein DIA quantification technique. The results showed that the protein content expression of MSCs-exosomes and MSCs-IEVs had a high overlap with that of the parent cells, and 170 proteins were specifically highly expressed in IEVs (FIG. 6A).

Figure 6B:
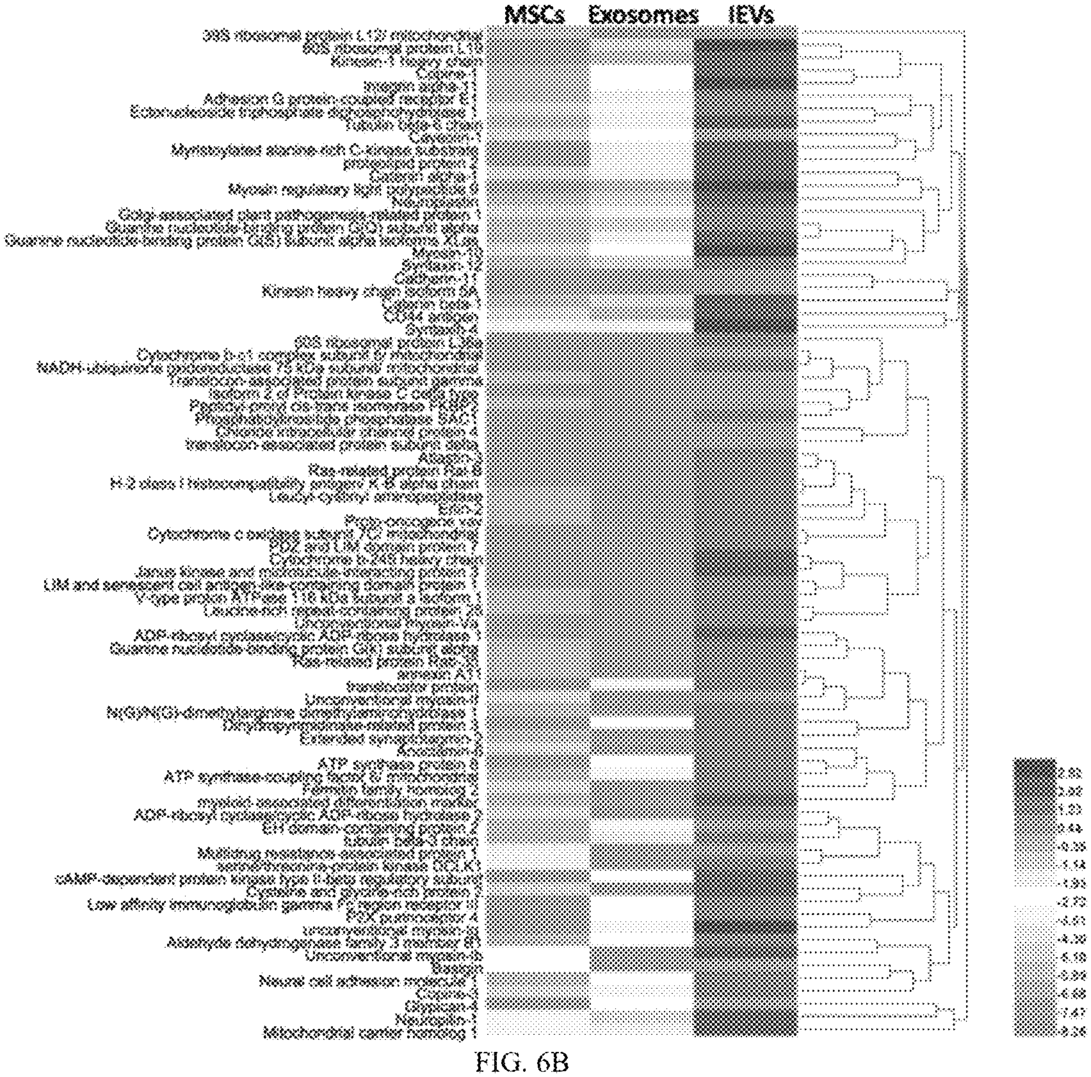
Figure 6C:
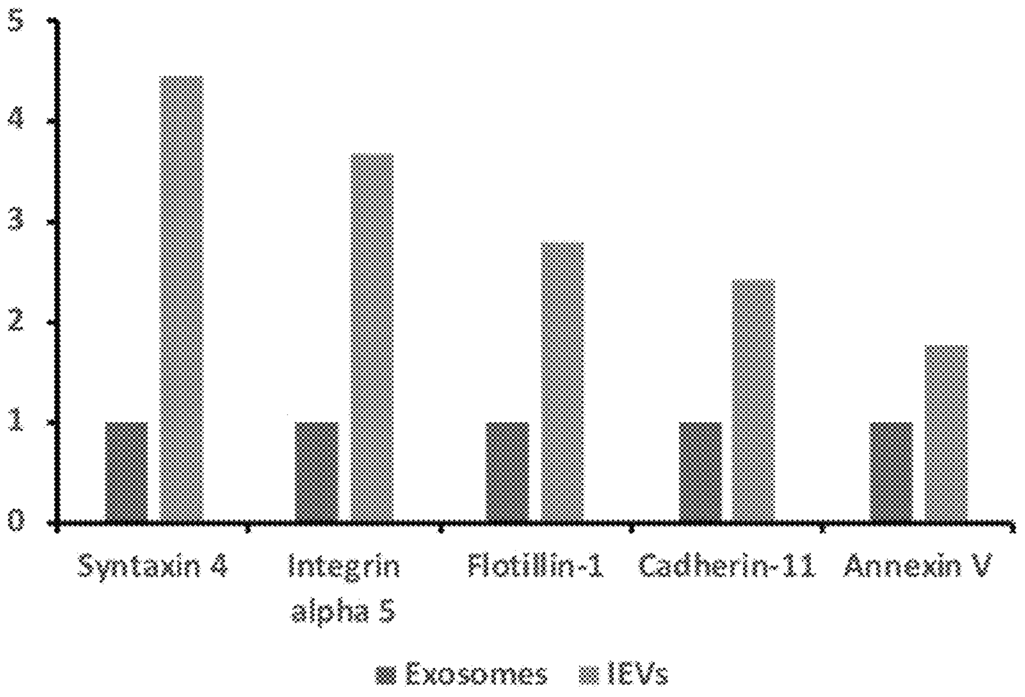
Figure 6D:
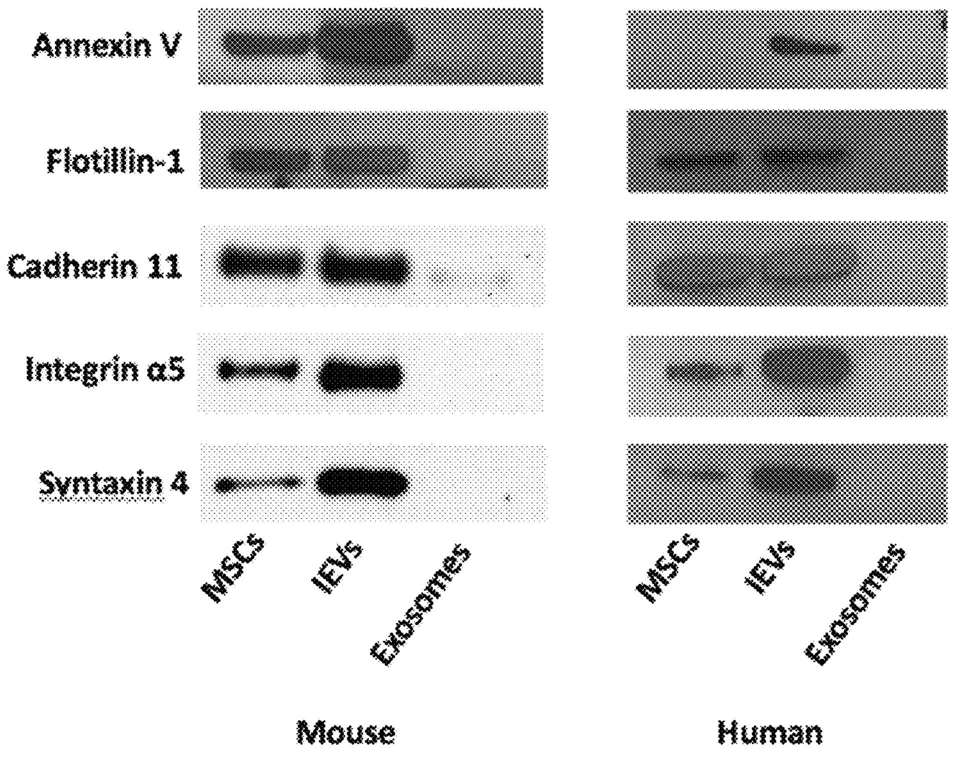

Through bioinformatics analysis, IEVs-specific and highly expressed proteins were screened, and a heat map was drawn (FIG. 6B). By further combining with GO enrichment analysis results of differential proteins, it is confirmed that IEVs can specifically express Annexin V, Flotillin-1, Cadherin 11, Integrin alpha 5, and Syntaxin 4 molecules at high levels. Compared with exosomes derived from the same MSCs, the expression levels of the 5 characteristic molecules of IEVs are all significantly up-regulated, specifically: the expression levels of the markers Annexin V, Flotillin-1, Cadherin 11, Integrin alpha 5, and Syntaxin 4 in IEVs are 1.76 fold, 2.81 fold, 2.41 fold, 3.68 fold and 4.45 fold, respectively, of that in exosomes (FIG. 6C). Finally, it was verified again with the Western Blot, and the results were consistent with the results of the DIA quantitative analysis (FIG. 6D).

MSCs-Exosomes: exosomes derived from BMMSCs.

MSCs-IEVs: IEVs derived from BMMSCs.

The MSCs in the content analysis and the MSCs for extraction of the exosomes and IEVs are from the same BMMSCs cell strain.

Example 4 Use of MSCs-Derived IEVs in Treating Mice with Bleeding Disorders, and Mechanistic Studies (1) Use of IEVs in Treating Mice with Hemophilia The in vitro procoagulant effects of the IEVs obtained in Example 2 and the exosomes extracted in Comparative Example 1 were examined using an in vitro clotting assay. The results, as shown in Table 3, showed that the IEVs shortened the in vitro coagulation time of most plasma, and the procoagulant effect was better than exosomes. However, for the plasma deficient in factors II, V, and X, the IEVs failed to exert the in vitro procoagulant effect, indicating that the in vitro procoagulant effect of IEVs was more concentrated at the upstream of the common coagulation pathway.

TABLE 3

| | Clotting time (min) | | | | | | | | |
|---|---|---|---|---|---|---|---|---|---|
| n = 5 | Mice plasma | Factor II deficient plasma | Factor V deficient plasma | Factor VII deficient plasma | Factor VIII deficient plasma | Factor IX deficient plasma | Factor X deficient plasma | Factor XI deficient plasma | Factor XII deficient plasma |
| PBS | 20 | >20 | >20 | >20 | >20 | >20 | >20 | >20 | >20 |
| IEVs | 0.75 | >20 | >20 | >17 | 2 | 4 | >20 | 4 | 4 |
| exosomes | 1.5 | >20 | >20 | >20 | 2.5 | 5 | >20 | 4 | 4 |

Figure 7:
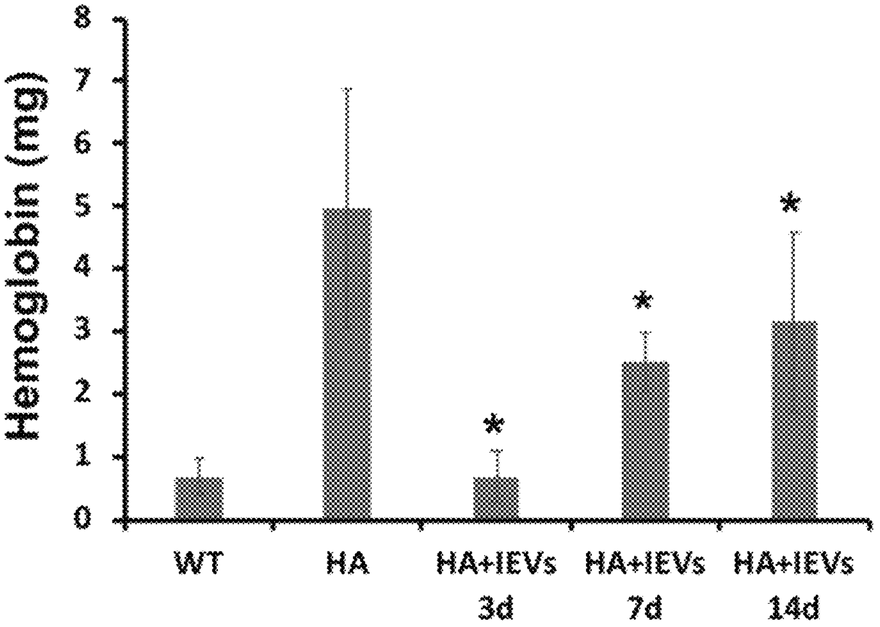
FIG. 7 shows the in vivo procoagulant effect of IEVs in hemophilia A mice.
Figure 8A:
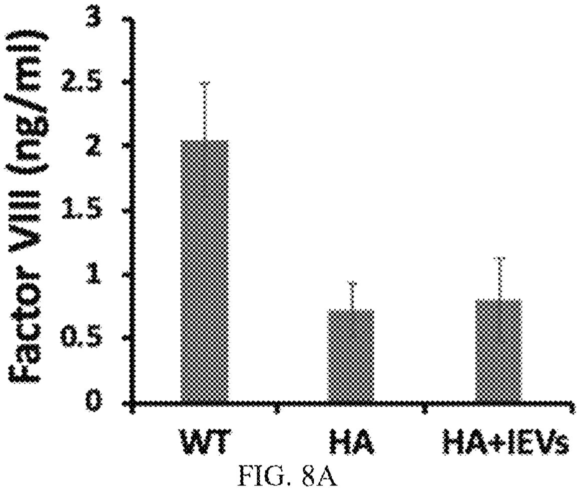
FIG. 8A-8D show changes in coagulation factor levels following IEVs injection in hemophilia A mice.
Figure 8B:
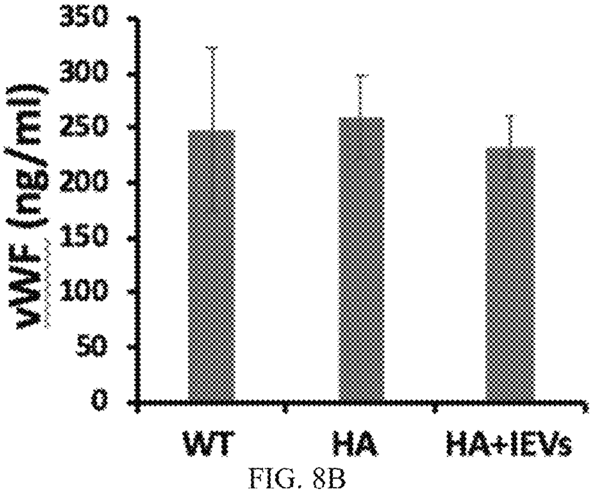
Figure 8C:
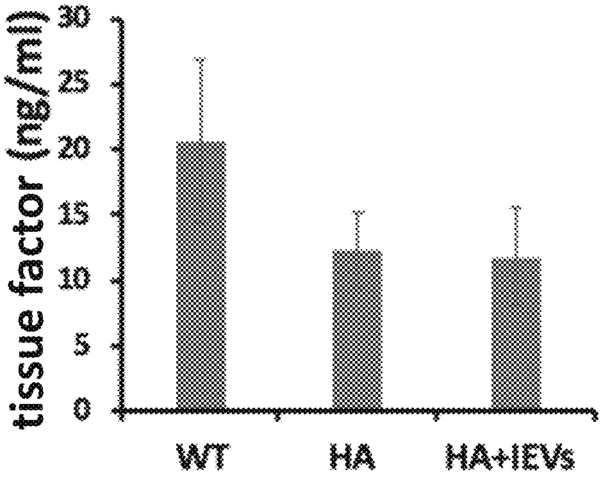
Figure 8D:
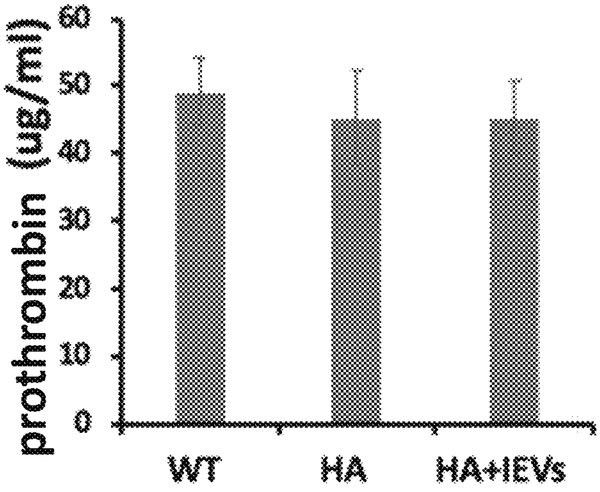

Mice with hemophilia A (clotting factor VIII deficiency) were used as a model to observe the procoagulant effect of IEVs in vivo by tail vein injection of $9\times10^8$ IEVs. As shown in FIG. 7, the treatment with IEVs significantly improved the bleeding tendency of mice with hemophilia, and the treatment effect was stably maintained for 14 days.

The results showed that IEVs could significantly promote coagulation in vitro. Besides, it can significantly improve the bleeding tendency after in vivo injection, and can be used to improve the bleeding tendency caused by hemophilia A.

The levels of various coagulation factors in the plasma of mice were also tested, and it was found that there were no significant changes in the coagulation factor VIII, vWF factor, tissue factor (TF) and prothrombin (FIG. 8A, FIG. 8B, FIG. 8C, and FIG. 8D).

Figure 9A:
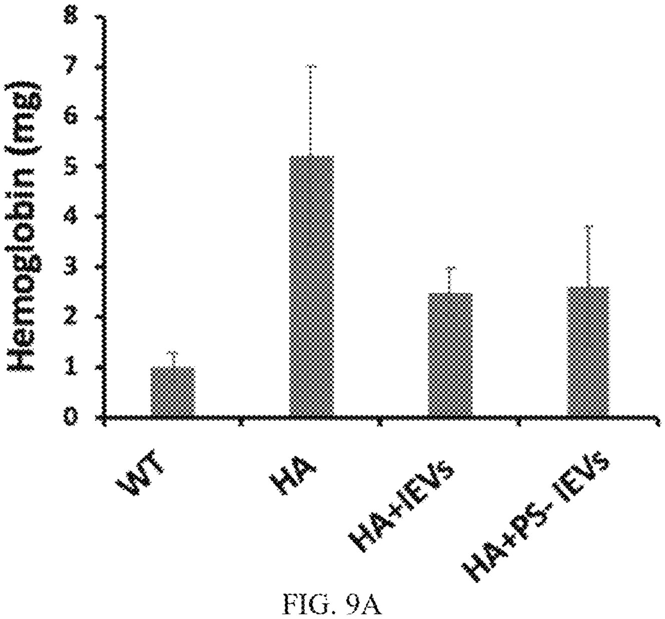
FIGS. 9A-9B show the impacts of blocking PS and TF of IEVs on in vivo treatment of IEVs in a hemophilia A mice model.
Figure 9B:
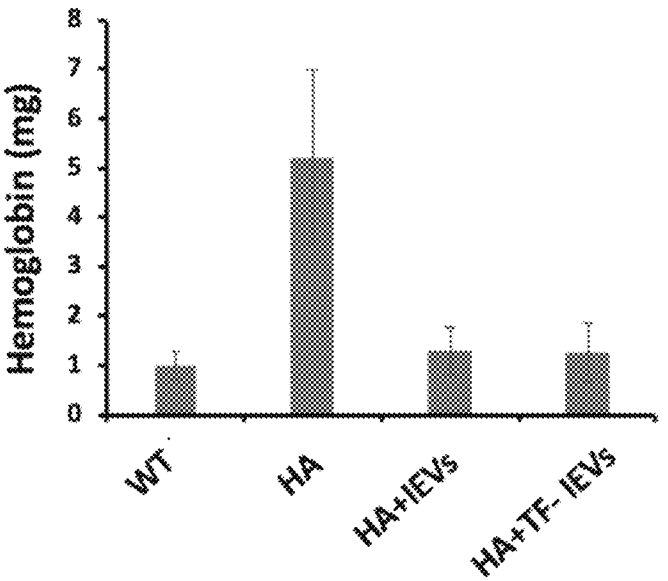

In the hemophilia A mice model, normal IEVs, PS-negative IEVs and TF-negative IEVs were separately injected, with a tail-cutting test performed 7 days later. As shown in FIG. 9A and FIG. 9B, the blocking of PS and TF did not affect the in vivo therapeutic effect of IEVs, suggesting that the mechanism of IEVs in treating hemophilia mice is not related to PS and TF. Previous literature reported that the procoagulant effect of extracellular vesicles was highly dependent on PS and TF on their surface, while the results of IEVs in vivo were inconsistent with previous studies, suggesting that IEVs may have a new procoagulant mechanism in the in vivo environment.

(2) Use of IEVs in Treating Mice with Lupus Bleeding

In clinical practice, patients with systemic lupus erythematosus (SLE) often have a bleeding tendency, the specific mechanism is unclear at present, and according the existing literature reports, it is mostly believed to be related to the factors such as thrombocytopenia associated with SLE. In the treatment measures, blood transfusion or platelet transfusion methods are often used, but the effect is not ideal.

Figure 9C:
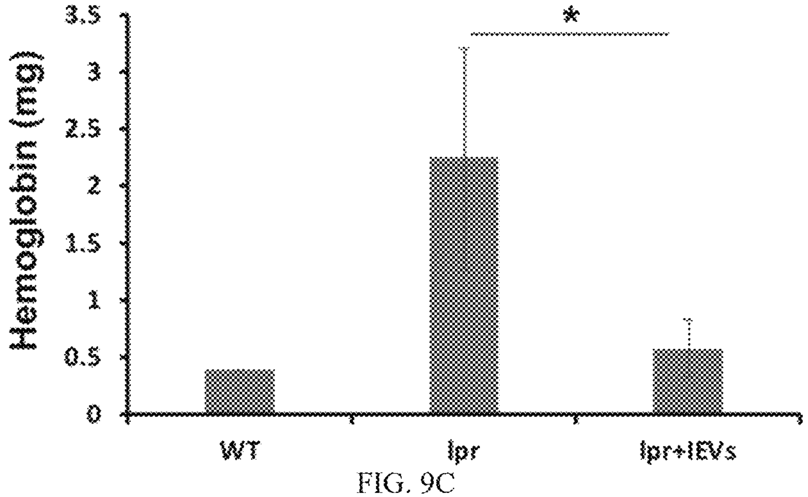
FIG. 9C shows that treatment of lpr mice with IEVs injection significantly improved the bleeding tendency of lpr mice.

According to the present invention, lpr mice were injected with IEVs (extracted in Example 2), and subjected to tail-cutting experiments 7 days later. The results showed that, the treatment with IEVs significantly improved the bleeding tendency of lpr mice, and the treatment effect was stably maintained for 7 days (FIG. 9C). The lpr mice are a representative animal model of SLE. The experimental results showed that IEVs could be used to improve the bleeding tendency of lupus erythematosus.

(3) Use of IEVs in Treating Mice with Chédiak-Higashi Syndrome

Chédiak-Higashi syndrome (CHS) is an autosomal recessive genetic disease, most of which is found in the offspring of consanguineous marriage. The pathogenic gene is the lysosomal trafficking regulator (LYST) gene. Mutations in the LYST gene often result in abnormal LYST protein production, which leads to platelet dysfunction. Patients may present with a significant bleeding tendency in clinical practice, and currently there is no effective preventive and therapeutic measures.

Figure 9D:
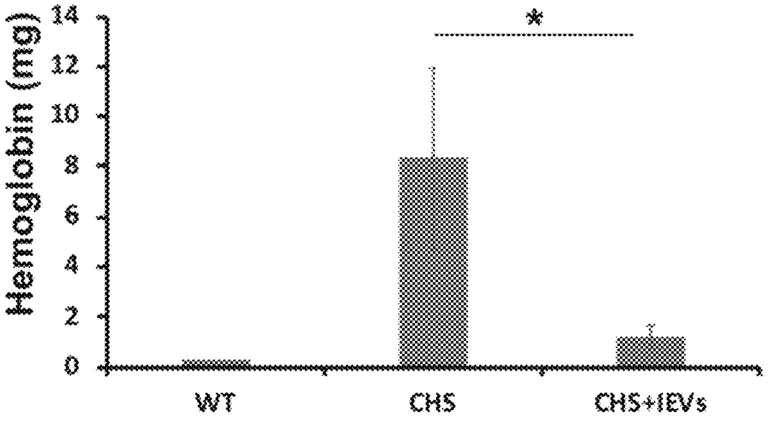
FIG. 9D shows that the treatment of CHS mice with IEVs injection significantly improved the bleeding tendency of CHS mice.

According to the present invention, the CHS mice were injected with IEVs (obtained in Example 2), and subjected to tail-cutting experiments 10 days later. The results showed that, the treatment with IEVs significantly improved the bleeding tendency of CHS mice, and the treatment effect was stably maintained for 10 days (FIG. 9D).

The results showed that IEVs could be used to improve the bleeding tendency of mice with Chédiak-Higashi syndrome.

Comparative Example 2

Figure 10:
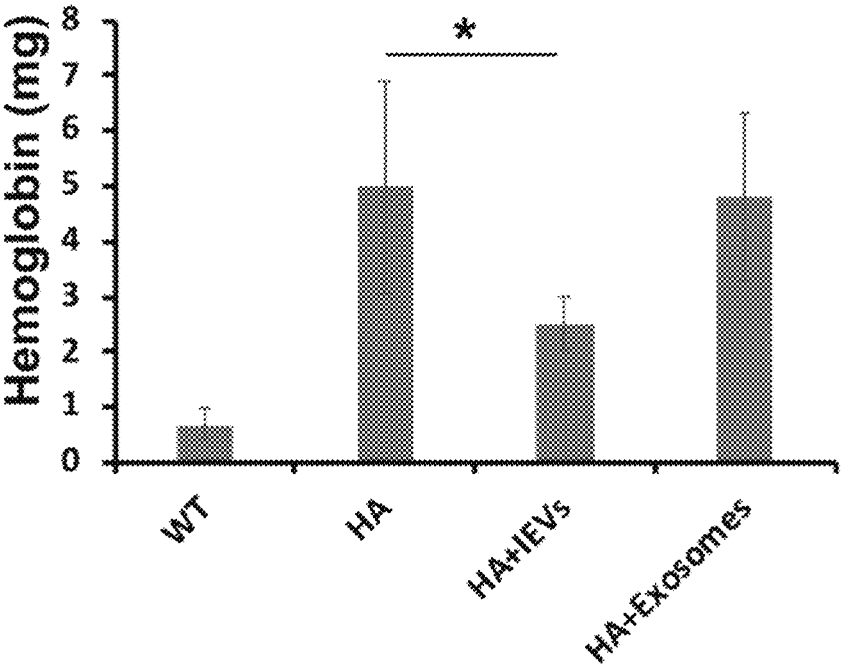
FIG. 10 shows a comparison of treatment of hemophilia A mice with IEVs and exosomes derived from the same MSCs source.

In the hemophilia A mice model, the IEVs (obtained in Example 2) and exosomes (extracted in Comparative Example 1) derived from the same MSCs were separately used for injection treatments ($9\times10^8$), and the results showed that the IEVs could significantly correct the bleeding tendency of mice, while the exosomes had no significant treatment effect (FIG. 10).

The in vitro procoagulant effect of the IEVs obtained in Example 2 was compared with that of the exosomes prepared in Comparative Example 1:

the IEVs obtained in Example 2 had a diameter in the range of 0.03 μm-0.2 μm and 0.2 μm-1 μm, and expressed the markers Syntaxin 4, Annexin V, Flotillin-1, Cadherin 11 and Integrin alpha 5, with a strong in vitro procoagulant effect; the exosomes prepared in Comparative Example 1 had a diameter of 0.03 μm-0.15 μm, and expressed the markers Complement C1q, Complement C3, Thrombospondin-1 and Thrombospondin-2, with a relatively weak in vitro procoagulant effect.

TABLE 4

| group | IEVs obtained in Example 2 | IEVs obtained in Example 2 | exosomes prepared in Comparative Example 1 |
|---|---|---|---|
| vesicle diameter | 0.03 μm-0.2 μm | 0.2 μm-1 μm | 0.03 μm-0.15 μm |
| markers expressed by vesicle | Syntaxin 4, Annexin V, Flotillin-1, Cadherin 11 and Integrin alpha 5 | Syntaxin 4, Annexin V, Flotillin-1, Cadherin 11 and Integrin alpha 5 | Complement C1q<br>Complement C3<br>Thrombospondin-1<br>Thrombospondin-2 |
| effects | strong in vivo and in vitro procoagulant effect | strong in vivo and in vitro procoagulant effect | weak in vivo and in vitro procoagulant effect |

Example 5

1. Culture of Induced Pluripotent Stem Cells (iPS Cells, iPSC)

(1) Lentivirus Preparation:

1 mL of DMEM was transferred to an EP tube, 5 μg of gene expression plasmid and 5 μg of g vsvg plasmid were added to 25 μL of liposomes, and the system was gently stirred at room temperature for 20 minutes. The mixture was added dropwise to cultured GP2-293 cells (95% mixed well) and vortexed to evenly distribute the mixture. The medium (DMEM+10% FBS+glutamine) was changed after 12 hours. After 24 hours of medium change, the medium containing the virus was collected, and after 48 hours the medium was collected again.

(2) Induction of Cellular Reprogramming:

Each well (12-well plate) was inoculated with $5\times10^5$ GP2-293 cells cultured in step (1) at 80% confluence. 100 ng of virus was added to the culture medium (DMEM+10% FBS (heat inactivated)+glutamine) of 500-1000 μL/well, 4 μg/mL polybrene was added, and a new culture medium was changed after incubation for 12 h. The steps were repeated. Within 7 days, $5\times10^4$ induced cells were inoculated into 10 cm dishes with feeder cells (mEFs). The next day, the medium was changed to an ES medium with bFGF (4 ng/mL), and the medium was changed every other day. Five days later, the cells started to clone, and if there were no ES-like clones after 40 days, it was considered to be failed.

(3) Cell Passage:

After 60% confluence, 0.5 mL of accutase was added to each dish and allowed to stand at room temperature for 1 minute. The separated cell aggregates were transferred to a 15 mL centrifuge tube, and an additional 2 mL mTeSR1 was used to collect any remaining aggregates. The rinse was added to the 15 mL tube. The 15 mL tube containing cell aggregates was centrifuged at 200 g for 5 minutes at room temperature. The supernatant was aspirated. The cells were resuspended while ensuring that the cells remain aggregated. Human iPS cells were assembled with mTeSR1 on new plates coated with Matrigel. The culture dish was placed in an incubator at 37° C., and quickly moved left and right to evenly distribute the movement of aggregates. Incubation was carried out at 37° C. with 5% carbon dioxide and 95% humidity. The fluid was changed every day.

2. Culture of MC3T3-E Subclone 14 Osteoblast Line

Purchased MC3T3-E1 Subclone 14 was thawed rapidly and centrifuged at 500 g for 5 min. The cell pellet at the bottom was collected after removing the supernatant. The cells were resuspended in a Dex (−) culture solution and inoculate on a 10 cm diameter cell culture dish at 37° C. in 5% $CO_2$. After full growth, trypsin was used for incubation and digestion at 37° C. for subculture and amplification, and then the Dex (−) culture medium was changed every 3 days. The cells could be used for multiple passages. The composition of the Dex (−) culture solution is shown in Table 5:

TABLE 5

Formunation Table of Dex (−) Culture Solution

| reagents | volume | final concentration |
|---|---|---|
| FBS | 100 mL | 20% |
| penicillin/streptomycin solution (10,000 U/mL) | 5 mL | 100 U/mL |
| glutamine (200 mM) | 5 mL | 2 mM |
| 2-ME (55 mM) | 500 μL | 55 μM |
| α-MEM | add to 500 mL | |

3. Analysis of IEVs

IEVs derived from osteoblast MC3T3-E1, iPS cells and human bone marrow mesenchymal stem cells (hBMMSCs) were compared. The three cell-derived IEVs were obtained as described in Example 2.

(1) Morphological Detection

As shown in FIG. 11, iPS cells (iPSCs) and osteoblast MC3T3-E1-derived IEVs, and human BMMSCs-derived IEVs were observed to be similar and irregular in morphology under a light microscope at 400×.

(2) Particle Diameter Detection of IEVs

Flow cytometry was performed, and the results were as shown in FIG. 12. The results of flow cytometry showed that the osteoblast line MC3T3-E1 and human bone marrow mesenchymal stem cells hBMMSCs-derived IEVs had the similar particle diameter distribution.

(3) Surface Marker Detection of IEVs

As shown in FIG. 13, with detection by the Western Blot method, the results showed that both the iPS cells (iPSCs) and human bone marrow mesenchymal stem cells hBMMSCs-derived IEVs showed high expression of the marker Anenexin V of IEVs. iPS cells-derived IEVs express Syntaxin 4 at a higher level than hBMMSCs.

Example 6 Excretion of IEVs Through the Skin and Hair $4\times10^6$ IEVs prepared in Example 2 was labeled with DIR, and resuspended in 200 μL of PBS, and then systemically injected into nude mice BALB/c-nu/nu through the tail veins. The distribution of IEVs on the skin surface was observed after 1, 3 and 7 days using a living body imaging instrument, and the results were as shown in FIGS. 13A-13C.

FIG. 13A showed that IEVs can reach the skin surface with the largest amount on Day 3, and substantially disappear on Day 7, indicating a dynamic metabolic process of IEVs on the skin surface (FIG. 13A). Immunofluorescence results showed that after systemic injection of C57 mice with PKH26-IEV, it gradually moved from the subcutaneous tissue to the dermis and epidermis over time. Large amounts of IEVs were observed on the stratum corneum at the skin surface on Day 7, suggesting that the systemically injected IEVs could be excreted as the stratum corneum sloughs off (FIG. 13B). Meanwhile, the presence of PKH26-IEV in hair follicles was found in hairs extracted from the surface of mice on day 7, indicating that the systemically injected IEVs were also metabolized as hairs fell off (FIG. 13C). This example demonstrates that IEVs can be excreted through the skin and hair, demonstrating the safety of injecting or increasing the level IEVs in the body.

Example 7

The culture of hiPSCs is the same as that in Example 5, and hUCMSCs is also a conventional culture method in the art.

The hiPSCs can be of the $26^{th}$-$29^{th}$ passage, but is not limited thereto, and the $26^{th}$ passage is specifically used in this example; the hUCMSCs may be of the $7^{th}$-$9^{th}$ passage, but is not limited thereto, and the $7^{th}$ passage is the specific used in this example.

1. Experiment Method (1) hiPSCs and hUCMSCs were induced to apoptosis for about 9 h using staurosporine (500 nM) (the other steps were the same as in Example 2), and stained with Annexin V (15 min) and 7AAD (3 min), and the rate of apoptosis was detected by flow cytometry.

(2) The IEVs from the supernatant of the apoptotic cells of step (1) were separated, and the expression rate of Annexin V was detected by flow cytometry. The IEVs were extracted by differential centrifugation, including the following steps: centrifugation at 800 g for 10 min—centrifugation at 2000 g for 5 min (other extraction steps are the same as in Example 2 except for this step)—centrifugation at 16000 g for 30 min—centrifugation at 16000 g for 30 min, to obtain IEVs.

Staining with Annexin V for 15 mins, and then performing the flow cytometry.

2. Experiment Results (1) We photographed the death process of hiPSCs and hUCMSCs with high content, and found that the two were have different death processes. hiPSCs contracted with multiple centers of the nucleus and cytoplasm, and then sent out dendritic branches with blebbing; while hUCMSCs contracted with a single center of the nucleus, accompanied by branching and blebbing. The results were as shown in FIG. 14.

(2) the apoptosis rates of hiPSCs and hUCMSCs induced to apoptosis were analyzed by flow cytometry, and it was demonstrated that most cells underwent apoptosis. The results were as shown in FIG. 15.

(3) The positive rate of Annexin 5 expression by flow cytometry was over 80% for both hiPSCs and hUCMSCs. The results were as shown in FIG. 16.

(4) The two types of IEVs were characterized using Nanoparticle Tracking Analysis (NTA):

1) As shown in FIG. 17, the particle size of IEVs derived from hiPSCs was about 100 nm, and the particle size of IEVs derived from hUCMSCs was about 180 nm;

2) As shown in FIG. 18, the yield of IEVs from hiPSCs was 21971 particles/hiPSCs, and the yield of hUCMSCs was 886 particles/hUCMSCs;

3) As shown in FIG. 19, the potential of IEVs derived from hiPSCs was about −12 mV, and the potential of IEVs derived from hUCMSCs was about −45 mV.

What is claimed is:

1. A method for detecting presence of an induced apoptotic mesenchymal stem cell vesicle in a sample, comprising:

detecting Syntaxin 4, Annexin V, Flotillin-1, Cadherin 11, or Integrin alpha 5 in the sample; and determining whether:

an expression level of the Annexin V in the sample is more than 1 to 2 fold of an expression level of Annexin V in an exosome, a migrant, a microbubble, or an ectosome;

an expression level of the Flotillin-1 in the sample is 2 to 3 fold of an expression level of Flotillin-1 in the exosome, the migrant, the microbubble, or the ectosome;

an expression level of the Cadherin 11 in the sample is more than 1 to 3 fold of an expression level of Cadherin 11 in the exosome, the migrant, the microbubble, or the ectosome;

an expression level of the Integrin alpha 5 in the sample is 3 to 4 fold of higher than an expression level of Integrin alpha 5 in the exosome, the migrant, the microbubble, or the ectosome; or an expression level of the Syntaxin 4 in the sample is 2 to 6 fold of higher than an expression level of Syntaxin 4 in the exosome, the migrant, the microbubble, or the ectosome.

2. The method of claim 1, wherein the sample and a cell from which the exosome, the migrant, the microbubble, or the ectosome derived are both mesenchymal stem cell.

3. The method of claim 1, wherein the sample and a cell from which the exosome, the migrant, the microbubble, or the ectosome derived are both bone marrow-derived mesenchymal stem cell.

4. The method of claim 1, comprising determining whether the expression level of the Annexin V in the sample is more than 1 to 2 fold of that in the exosome, the migrant, the microbubble, or the ectosome.

5. The method of claim 1, comprising determining whether the expression level of the Flotillin-1 in the sample is 2 to 3 fold of that in the exosome, the migrant, the microbubble, or the ectosome.

6. The method of claim 1, comprising determining whether the expression level of the Cadherin 11 is more than 1 to 3 fold of that in the exosome, the migrant, the microbubble, or the ectosome.

7. The method of claim 1, comprising determining whether the expression level of the Integrin alpha 5 in the sample is 3 to 4 fold of higher than that in the exosome, the migrant, the microbubble, or the ectosome.

8. The method of claim 1, comprising determining whether the expression level of the Syntaxin 4 in the sample being is 2 to 5 fold of that in the exosome, the migrant, the microbubble, or the ectosome.

9. The method of claim 1, comprising determining whether the expression level of the Annexin V in the sample is 1.5 to 2 fold, the expression level of the Flotillin-1 in the sample is 2.5 to 3 fold, the expression level of the Cadherin 11 in the sample is 1.5 to 2.5 fold, the expression level of the Integrin alpha 5 in the sample is 3.5 to 4 fold, or the expression level of the Syntaxin 4 in the sample is 3.5 to 5 fold of that in the exosome, the migrant, the microbubble, or the ectosome.

10. The method of claim 1, comprising determining whether the expression level of the Annexin V in the sample is 1.5 to 1.9 fold, the expression level of the Flotillin-1 in the sample is 2.5 to 2.9 fold, the expression level of the Cadherin 11 in the sample is 1.8 to 2.5 fold, the expression level of the Integrin alpha 5 in the sample is 3.5 to 3.9 fold, or the expression level of the Syntaxin 4 in the sample is 4 to 5 fold of that in the exosome, the migrant, the microbubble, or the ectosome.

11. The method of claim 10, comprising determining whether the expression level of the Annexin V in the sample is 1.5 to 1.9 fold of that in the exosome, the migrant, the microbubble, or the ectosome.

12. The method of claim 10, comprising determining whether the expression level of the Flotillin-1 in the sample is 2.5 to 2.9 fold of that in the exosome, the migrant, the microbubble, or the ectosome.

13. The method of claim 10, comprising determining whether the expression level of the Cadherin 11 is 1.8 to 2.5 fold of that in the exosome, the migrant, the microbubble, or the ectosome.

14. The method of claim 10, comprising determining whether the expression level of the Integrin alpha 5 in the sample is 3.5 to 3.9 fold of that in the exosome, the migrant, the microbubble, or the ectosome.

15. The method of claim 10, comprising determining whether the expression level of the Syntaxin 4 in the sample is 4 to 5 fold of that in the exosome, the migrant, the microbubble, or the ectosome.

16. The method of claim 2, wherein the induced apoptotic mesenchymal stem cell vesicle is derived from mesenchymal stem cell by inducing apoptosis of the mesenchymal stem cell in a presence of staurosporine, ultraviolet irradiation, starvation, or thermal stress, or a combination thereof.

* * * * *